(12) United States Patent
Duncan et al.

(10) Patent No.: US 12,431,244 B2
(45) Date of Patent: Sep. 30, 2025

(54) INTERPRETABLE DEEP MACHINE LEARNING FOR CLINICAL RADIOLOGY

(71) Applicant: Yale University, New Haven, CT (US)

(72) Inventors: James S. Duncan, Madison, CT (US); Brian Letzen, Orange, CT (US); Julius Chapiro, New Haven, CT (US); Clinton Wang, New Haven, CT (US)

(73) Assignee: Yale University, New Haven, CT (US)

( * ) Notice: Subject to any disclaimer, the term of this patent is extended or adjusted under 35 U.S.C. 154(b) by 656 days.

(21) Appl. No.: 17/265,862

(22) PCT Filed: Aug. 7, 2019

(86) PCT No.: PCT/US2019/045571
§ 371 (c)(1),
(2) Date: Feb. 4, 2021

(87) PCT Pub. No.: WO2020/033594
PCT Pub. Date: Feb. 13, 2020

(65) Prior Publication Data
US 2021/0174154 A1 Jun. 10, 2021

Related U.S. Application Data

(60) Provisional application No. 62/715,647, filed on Aug. 7, 2018.

(51) Int. Cl.
*G16H 50/20* (2018.01)
*G06F 18/21* (2023.01)
(Continued)

(52) U.S. Cl.
CPC ............. *G16H 50/20* (2018.01); *G06F 18/21* (2023.01); *G06F 18/22* (2023.01);
(Continued)

(58) Field of Classification Search
CPC ........ G16H 50/20; G16H 30/40; G16H 50/70; G06F 18/21; G06F 18/22;
(Continued)

(56) References Cited

U.S. PATENT DOCUMENTS 6,968,327 B1  11/2005  Kates et al.
8,775,341 B1   7/2014  Commons
(Continued)

OTHER PUBLICATIONS

International Search Report and Written Opinion, International Patent Application No. PCT/US2019/045571, Oct. 18, 2019.
(Continued)

*Primary Examiner* — Qian Yang
(74) *Attorney, Agent, or Firm* — Saul Ewing LLP; Sean J. D.; Kathryn Doyle

(57) ABSTRACT

One aspect of the invention provides a computer-implemented method of identifying one or more clinical factors associated with an artificial intelligence prediction. The computer implemented method includes: applying a previously trained deep neural network to one or more images for a subject to produce a prediction, the previously trained deep neural network comprising a plurality of nodes; comparing outputs of the nodes to previously identified patterns of node outputs for a plurality of individual clinical factors; and identifying which of the plurality of individual clinical factors are most correlated with the outputs of the nodes.

5 Claims, 17 Drawing Sheets

(51) Int. Cl.

| | |
|---|---|
| *G06F 18/22* | (2023.01) |
| *G06F 18/2413* | (2023.01) |
| *G06F 18/2415* | (2023.01) |
| *G06F 18/2431* | (2023.01) |
| *G06N 3/04* | (2023.01) |
| *G06N 3/08* | (2023.01) |
| *G06T 5/77* | (2024.01) |
| *G06T 7/00* | (2017.01) |
| *G06T 11/00* | (2006.01) |
| *G16H 30/40* | (2018.01) |
| *G16H 50/70* | (2018.01) |

(52) U.S. Cl.
CPC .... *G06F 18/24147* (2023.01); *G06F 18/2415* (2023.01); *G06F 18/2431* (2023.01); *G06N 3/04* (2013.01); *G06N 3/08* (2013.01); *G06T 5/77* (2024.01); *G06T 7/0012* (2013.01); *G06T 11/00* (2013.01); *G16H 30/40* (2018.01); *G16H 50/70* (2018.01); *G06T 2207/20084* (2013.01); *G06T 2207/30096* (2013.01); *G06V 2201/03* (2022.01)

(58) Field of Classification Search
CPC ........... G06F 18/24147; G06F 18/2415; G06F 18/2431; G06N 3/04; G06N 3/08; G06N 3/045; G06N 3/048; G06N 3/047; G06N 5/045; G06N 3/082; G06N 3/088; G06N 7/01; G06T 5/005; G06T 7/0012; G06T 11/00; G06T 2207/20084; G06T 2207/30096; G06V 2201/03; G01N 2800/60

See application file for complete search history.

(56) References Cited

U.S. PATENT DOCUMENTS

| | | |
|---|---|---|
| 2006/0154276 A1 | 7/2006 | Lois et al. |
| 2007/0106537 A1 | 5/2007 | Moore |
| 2016/0292855 A1* | 10/2016 | Metzger ................ G06T 7/0012 |
| 2018/0068083 A1 | 3/2018 | Cohen et al. |

OTHER PUBLICATIONS

Wikipedia, Convolutional neural network, https://en.wikipedia.org/wiki/Convolutional_neural_network, downloaded Jun. 20, 2018, 21 pages.

Wikipedia, Multilayer perceptron, https://en.wikipedia.org/wiki/Multilayer_perceptron, downloaded Jul. 19, 2018, 4 pages.

Hamm, C. A., et al., "Deep learning for liver tumor diagnosis part 1: development of a convolutional neural network classifier for multi-phasic MRI", European Radiology 29, 2019, 3338-3347.

Lee, J , et al., "Deep Learning in Medical Imaging: General Overview", Korean J Radiol 18(4), 2017, 570-584.

Wang, C. J., et al., "Deep learning for liver tumor diagnosis part II: convolutional neural network interpretation using radiologic imaging features", European Radiology 29, 2019, 3348-3357.

* cited by examiner

| Contrast-Enhanced T1-w MRI | Labeled Radiological Feature | Contrast-Enhanced T1-w MRI | Labeled Radiological Feature |
|---|---|---|---|
| Arterial Venous Delayed | Hepatic lesion classes that typically exhibit the feature | Arterial Venous Delayed | Hepatic lesion classes that typically exhibit the feature |
| | Arterial phase enhancement<br>FNH, HCC | | Infiltrative appearance<br>ICC |
| | Central scar<br>FNH | | Isointense in venous and delayed phase<br>FNH |
| | Enhancing rim<br>CRC metastasis } Grouped into a single feature | | Nodularity<br>ICC |
| | Capsule/pseudocapsule<br>HCC | | Nodular/discontinuous peripheral enhancement<br>Cavernous hemangioma |
| | Heterogeneous lesion<br>ICC, HCC (OPTN5B(X)) | | Progressive centripetal filling<br>Cavernous hemangioma |
| | Hyperenhancing mass in delayed phase<br>Cavernous hemangioma | | Progressive enhancement<br>CRC metastasis, ICC |
| | Hypoenhancing core<br>CRC metastasis } Grouped into a single feature | | Thin-walled<br>Cyst |
| | Hypoenhancing mass<br>Cyst | | Washout<br>HCC |

FIG. 13

INTERPRETABLE DEEP MACHINE LEARNING FOR CLINICAL RADIOLOGY

CROSS-REFERENCE TO RELATED APPLICATIONS

This application is a national phase application under 35 U.S.C. § 371 of International Application No. PCT/US2019/045571, filed Aug. 7, 2019, which claims the benefit of priority to U.S. Provisional Patent Application Ser. No. 62/715,647, filed Aug. 7, 2018. The entire content of this each application is hereby incorporated by reference herein.

BACKGROUND OF THE INVENTION

There has been explosive growth in artificial intelligence/deep machine learning applied to the field of medicine. Most artificial intelligence (AI) approaches for radiology involve detection or classification of radiological findings, but do not provide any justification or reasoning for how these systems and approaches arrive at predictions, creating a "black box". This is a significant barrier to clinical acceptance from physicians and, thus, successful translation and adoption into clinical use. A major concern is that a software algorithm could inadvertently cause harm to patients, such as recommending to send a patient to surgery due to a mistake/artifact.

Advancements in convolutional neural networks (CNNs) have shown the potential for deep learning techniques to revolutionize the current process of radiological diagnosis. A synergistic workflow that combines the experience of radiologists and the computational power of artificial intelligence systems may remarkably improve the efficiency and quality of clinical care. Although CNNs demonstrate superior performance, their "black box" design limits their clinical adoption. In the current form, they do not provide information about the factors used in decision-making, which can prevent radiologists and other physicians from incorporating a CNN's results into an informed decision-making process. This is particularly important as many imaging-based models do not integrate other factors that may be pertinent to a diagnosis, such as clinical and genetic data. CNNs' inability to explain their reasoning also leads to a lack of safeguards and accountability when they fail.

SUMMARY OF THE INVENTION

One aspect of the invention provides a computer-implemented method of identifying one or more clinical factors associated with an artificial intelligence prediction. The computer-implemented method includes: applying a previously trained deep neural network to one or more images for a subject to produce a prediction, the previously trained deep neural network comprising a plurality of nodes; comparing outputs of the nodes to previously identified patterns of node outputs for a plurality of individual clinical factors; and identifying which of the plurality of individual clinical factors are most correlated with the outputs of the nodes.

This aspect of the invention can have a variety of embodiments. The previously identified patterns of node outputs for a plurality of individual clinical factors can have been generated by applying the previously trained deep neural network to one or more images having a single clinical factor.

The computer-implemented method can further include generating a contribution score for one or more of the plurality of individual clinical factors. The generating the contribution score step can further include: iteratively removing one or more of the multilayer nodes associated with the previously identified patterns of node outputs for one of the plurality of individual clinical factors from the previously trained deep neural network to produce an altered deep neural network; applying the altered deep neural network to the one or more images to produce an altered prediction; and identifying a difference between the altered prediction and the prediction. The generating the contribution score step can further include: quantifying the impact of removing the multilayer nodes associated with the previously identified patterns of node outputs for one of the plurality of individual clinical factors. The generating the contribution score step can further include: quantifying the impact of removing one or more images having a single clinical factor on the prediction of the deep neural network.

The computer-implemented method can further include: generating one or more altered images illustrating regions of the one or more images associated with the one or more individual clinical factors correlated with the outputs of the multilayer nodes. The generating one or more altered images step can further include: identifying which of the multilayer node outputs are most correlated with each clinical factor; comparing the multilayer node outputs for the one or more images used for prediction relative to the multilayer node outputs for the one or more images correlated with individual clinical factors; designating each pixel or voxel in the one or more images used for prediction as significant to the one or more individual clinical factors if the multilayer node outputs associated with the pixel or voxel are correlated with the individual clinical factors and are comparable to the multilayer node outputs found in the one or more images correlated with individual clinical factors; and applying an overlay for each of the one or more individual clinical factors corresponding to the pixels or voxels designated as significant to the individual clinical factor. The generating one or more altered images step can further include: iteratively removing one or more pixels or voxels from the one or more images to generate one or more stripped images; reapplying the previously trained deep neural network to the one or more stripped images; identifying one or more differences in outputs of the multilayer nodes for the one or more stripped images relative to the outputs of the multilayer nodes for the one or more images; comparing the one or more differences to the previously identified patterns of node outputs for the plurality of individual clinical factors; designating a pixel or voxel as associated with the one or more individual clinical factors correlated with the outputs of the multilayer nodes if the differences are correlated with the previously identified patterns of node outputs for the plurality of individual clinical factors; and applying an overlay corresponding to the pixels or voxels designated as associated with the one or more individual clinical factors.

BRIEF DESCRIPTION OF THE DRAWINGS

FIG. 13 depicts examples of labeled example lesions for the 14 radiological features.

DETAILED DESCRIPTION

Definitions

Figure 1:
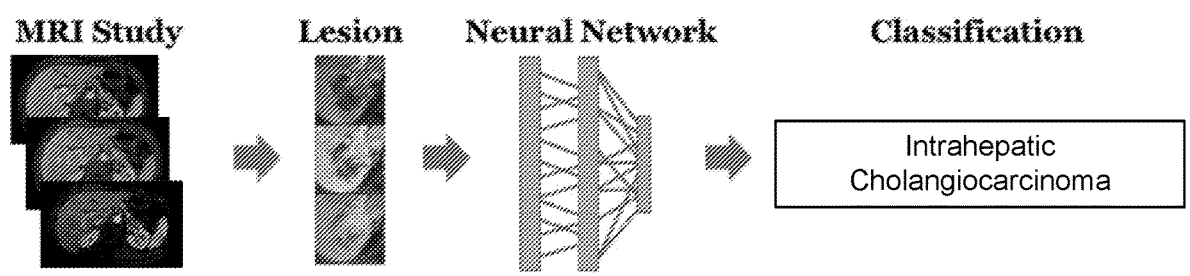
FIG. 1 depicts an exemplary process of classifying a radiological lesion after developing and training a neural network.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "node" as used herein, may refer to an artificial neuron, node, perceptron, multi-layer perceptron, filter, and the like, of a neural network, deep neural network, convolutional neural network, capsule network, and the like. "Node" may also describe an algorithm for supervised learning of binary classifications, a type of linear classifier, such as a classification algorithm that makes predictions based on a linear predictor function combining a set of weights with a vector feature.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides computer-implemented deep learning systems and methods for identifying and classifying one or more clinical factors in a medical (e.g., radiological) image that may be associated with one or more clinical factors that may be associated with one or more normal physiologies and/or pathophysiologies. The systems and methods of the present invention generate one or more interpretable artificial intelligence (AI) predications utilizing the inner layers of deep-learning models while providing logical justification for the generated predications. In certain embodiments, the methods of the present invention utilize one or more trained deep-learning AI systems Embodiments of the present invention provide a summary of high-level features that can be used by clinicians to understand the rationale leading to a given prediction.

Embodiments of the present invention provide systems that utilize a deep neural network (DNN) trained to perform a radiologically relevant classification task, for example, the classification of hepatic lesions from 3D abdominal contrast-enhanced magnetic resonance images (shown in FIGS. 1-3 and FIG. 7). Embodiments of the present invention may include deep neural networks, convolutional neural networks, capsule networks, and the like.

Figure 16:
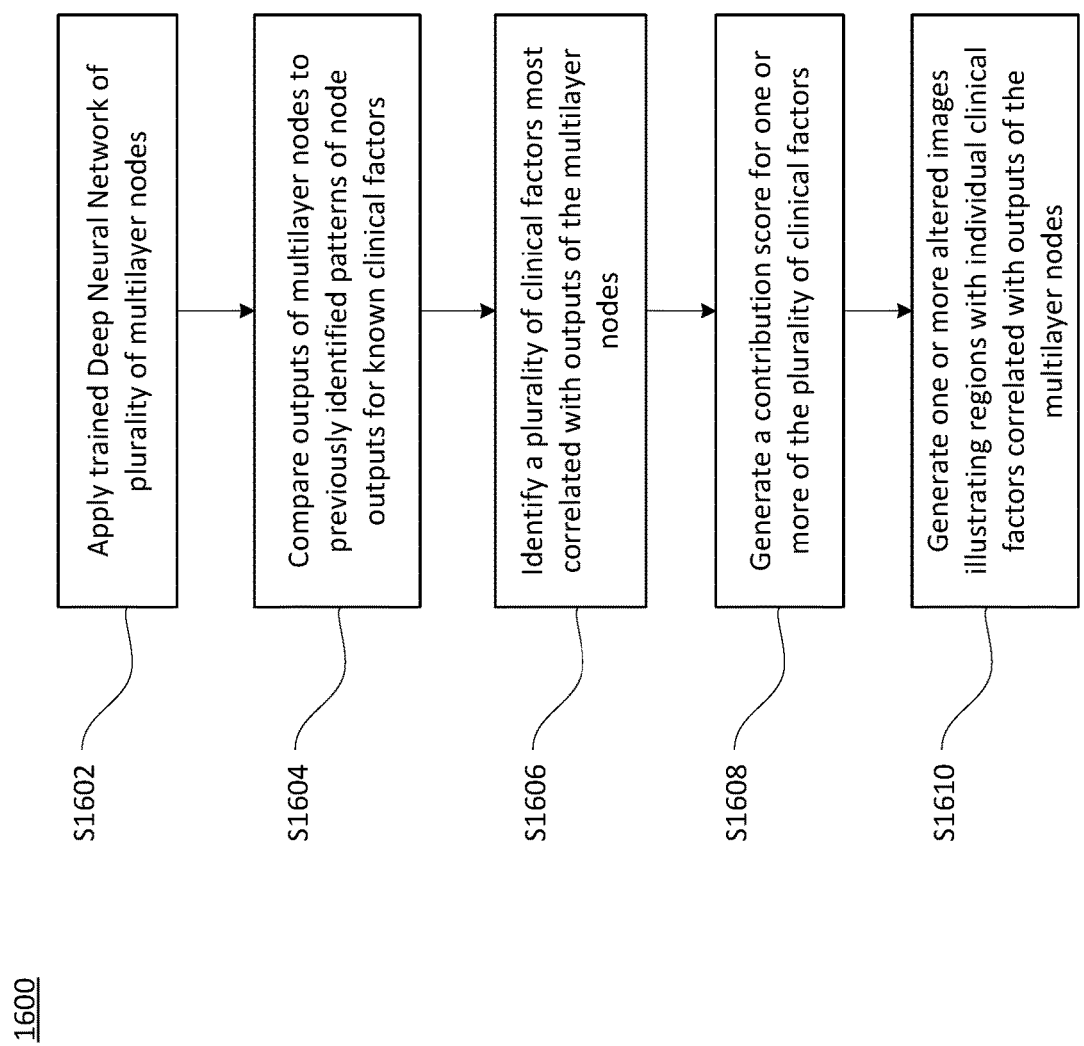
FIG. 16 depicts an exemplary method of the present invention.

Referring now to FIG. 16, embodiments of exemplary methods 1800 of the present invention for identifying and/or classifying one or more clinical factors in subject using radiological images is shown.

Figure 8:
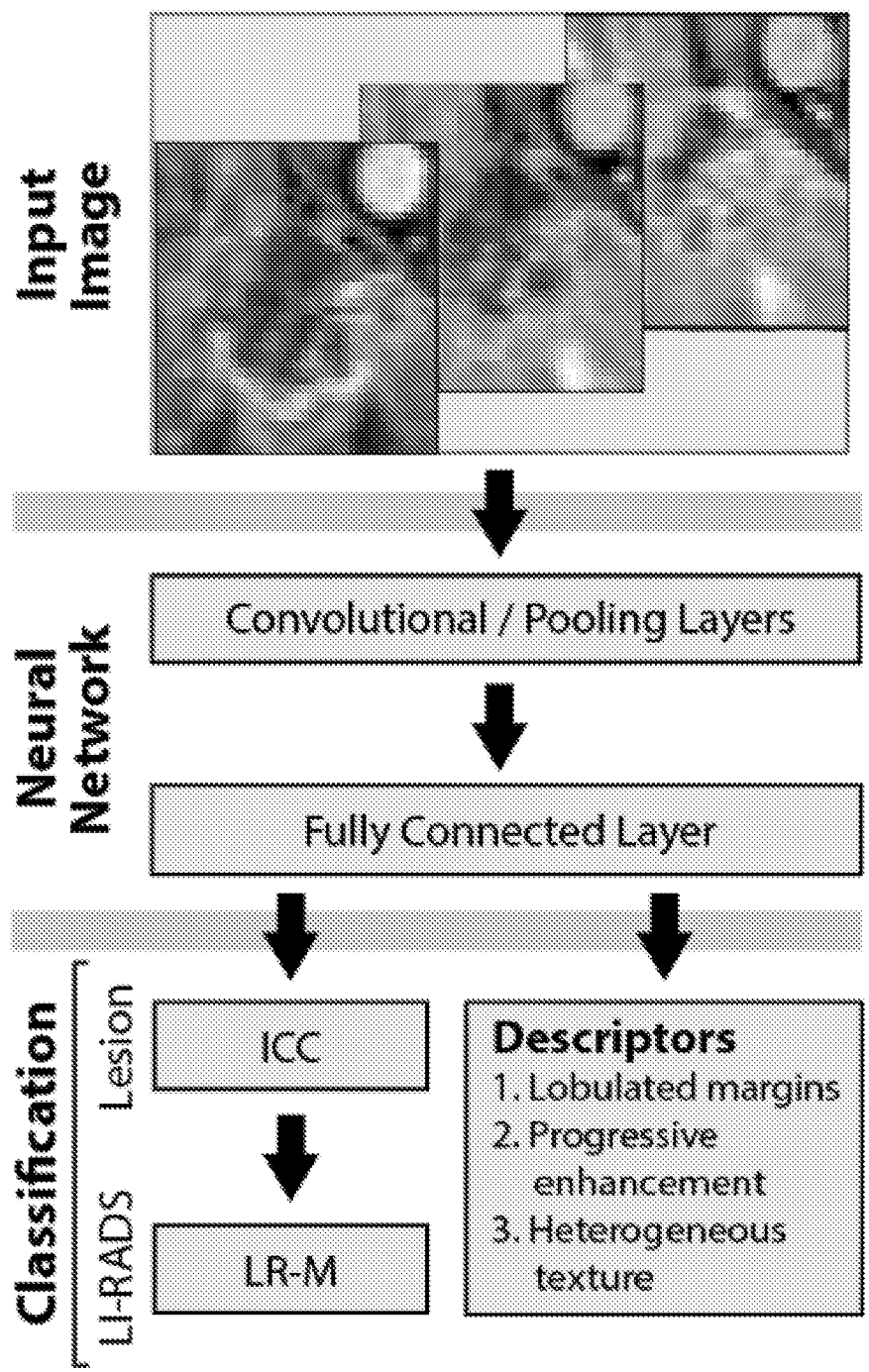
FIG. 8 illustrates exemplary convolutional neural network (CNN) model architecture used to infer the lesion entity and radiological features based on the input image, shown for an example of intrahepatic cholangiocarcinoma. The LI-RADS classification follows from the lesion class.

In step S1602, a trained deep neural network having plurality of multilayer nodes can be applied to one or more radiological images for a subject to produce a prediction. The one or more radiological images may include, for example magnetic resonance (MR) images including three-dimensional, contrast-enhanced MR images. The one or more radiological images may include, for example, images having a single clinical factor. Embodiments of the deep neural network may consist of multiple convolutional, pooling, and/or fully connected layers, and the like (as shown in FIG. 8). The deep neural network may include a plurality of multilayer nodes, perceptrons, filters, artificial neurons, and the like.

The deep neural network may be trained by one or more processes of training a deep learning AI system. For example, the process may include: (1) programming a basic model such as, for example, a neural network of several complex layers; (2) providing large amounts of input training data (e.g. images of benign lesions and malignant tumors) and output classification data (e.g. labels of "benign" or "malignant" for each image); and (3) running a training algorithm on this model/data. This process may result in trained values to one or more layers of the network, so that when a new input is presented, the model can predict the output.

In some embodiments, the subject is a mammalian subject, for example, a human, a dog, sheep, horse, cow, goat, pig, mouse, rat, cat, and the like. The subject may include a non-mammalian subject.

In step S1604, one or more outputs of the multilayer node can be compared to previously identified patterns of node outputs for known clinical factors. The clinical factors may include, for example, hepatic lesions such as hepatocellular carcinoma (HCC), simple cysts, cavernous hemangioma, focal nodular hyperplasia (FNH), intrahepatic cholangiocarcinoma (ICC), colorectal cancer (CRC) metastasis, among others. In some embodiments, sets of labeled radiological features with a plurality of example image sets per feature are used. The values of the hidden nodes of the one or more deep neural network may then be stored. The distribution of stored hidden unit values for each feature may then be estimated (e.g., as shown in FIG. 131, Panel (A)). When a new test image is passed through the model, the distribution pattern of the hidden unit values may be compared with the distribution pattern for each feature type.

Figure 9:
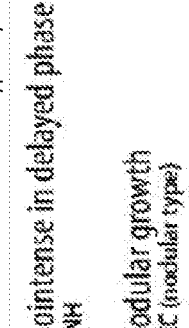
FIG. 9 depicts examples of labeled example lesions for each of the 16 radiological features.
Figure 10:
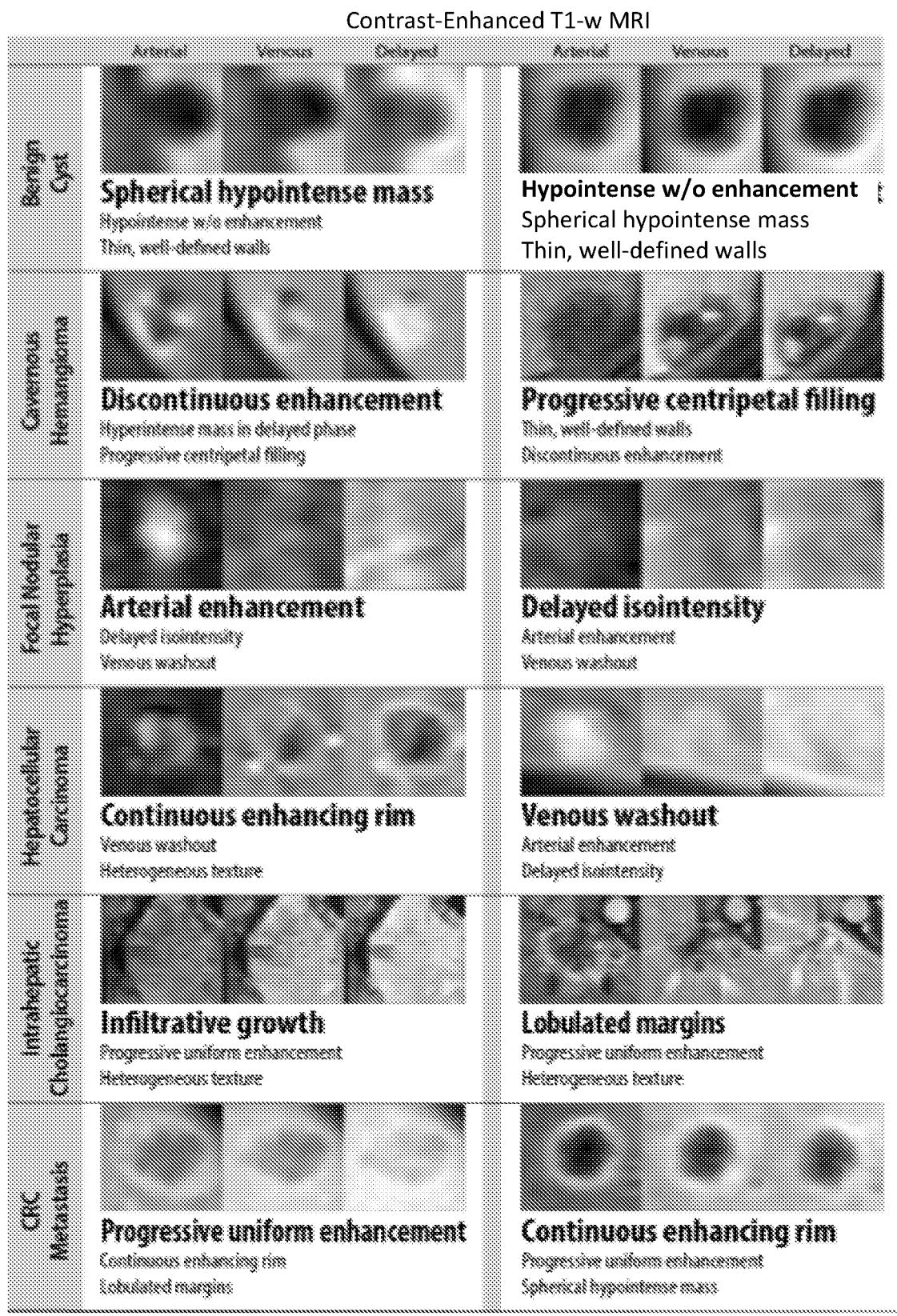
FIG. 10 depicts the top three descriptors output by the CNN model for sample test images, ranked by confidence level. The model is able to differentiate between common features within each lesion class.
Figure 11:
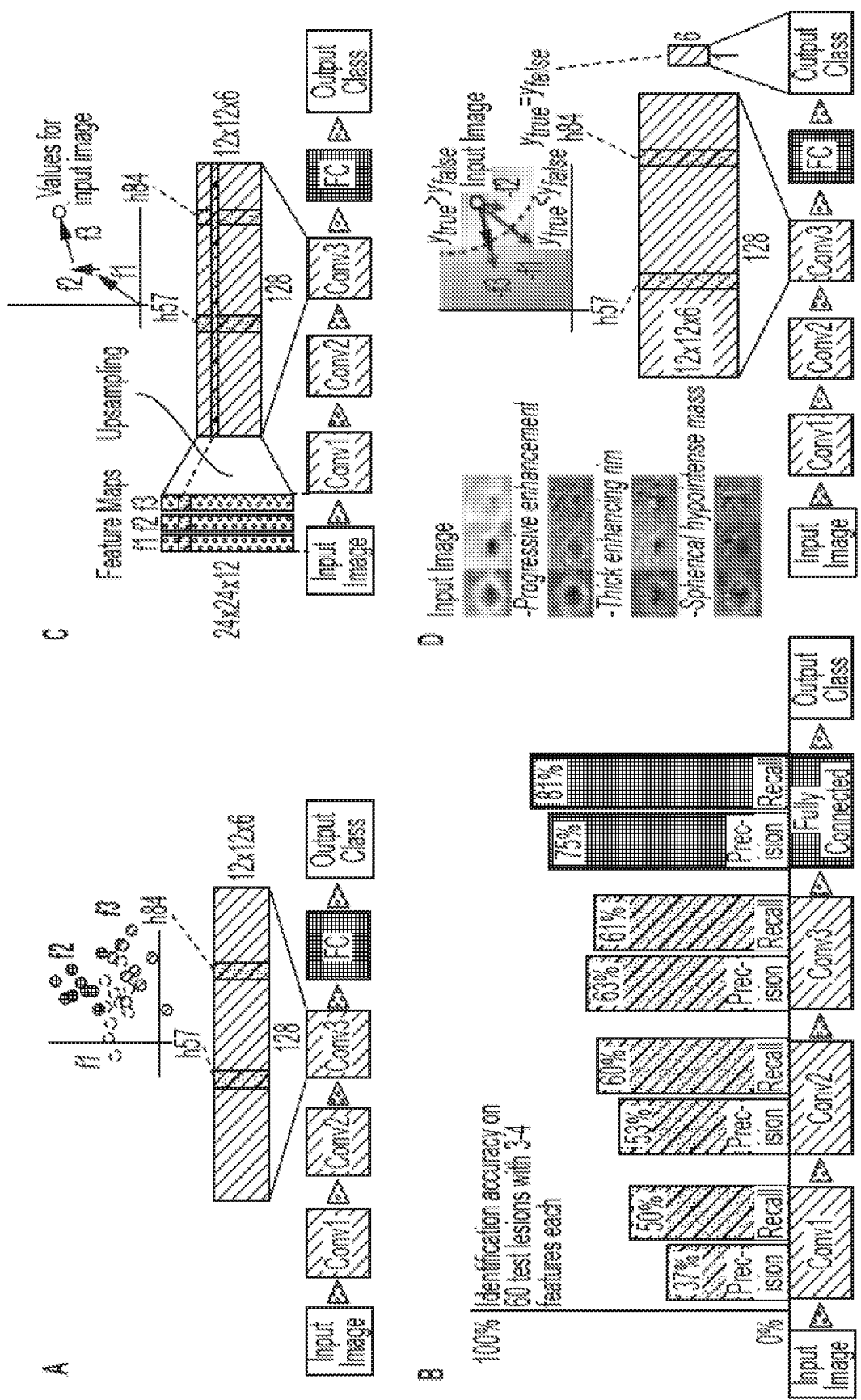
FIG. 11, comprising Panels (A) through (D), diagrams an exemplary interpretable AI approach. Panels (A) and (B) depict feature extraction, which includes identifying radiological features in the image. Panel (C) depicts feature mapping, which includes identifying where these features are found in the image. Panel (D) depicts feature relevance, which includes quantifying each feature's contribution to the model's decision.

In step S1606, one or more clinical factors most correlated with outputs of the multilayer nodes can be identified. In some embodiments, a small set of labelled examples of different radiological features is presented to the trained model (shown in FIGS. 9-10). In certain embodiments, representative features of a given test image are selected as those demonstrating high correlation with the original distribution patterns (as shown in FIG. 11, Panel (B)). In some embodiments, the location of where features are found within an image may be resolved. The mapping between the hidden units of the network and the voxels of the input data may be determined by working backwards. This mapping may be achieved with techniques including, for example, matrix factorization between the hidden units and identified features. These factorized units may subsequently mapped to voxels of the input image. A segmented feature map may then be generated by applying a threshold to the values in an original lesion space. In some embodiments, the segmented feature map may be visually superimposed on a lesion image, for example, as shown in FIG. 11, Panel (C).

In step S1608, a contribution score can be generated for one or more of the plurality of clinical factors in order to determine which features are most relevant to the model's classification decision. Embodiments of this step include iteratively removing or more of the multilayer nodes associated with the previously identified patterns of node outputs for one of the plurality of individual clinical factors from the previously trained deep neural network to produce an altered deep neural network. The altered deep neural network may then be applied to the one or more images in order to produce an altered predication. A difference may then be identified between the altered predication and the prediction. In some embodiments, factorized units may be used in order to estimate the margin for misclassification when features are absent. The relative decrease in the misclassification margin may then be used to assign a relevance score to each feature (e.g. shown in FIG. 11, Panel (D)).

Embodiments of generating a contribution score may include quantifying the impact of removing the multilayer nodes associated with the previously identified patterns of node outputs for one or more of the plurality of individual clinical factors.

Embodiments of generating a contribution score may include quantifying the impact of removing one or more images having a single clinical factor on the prediction of the deep neural network.

In step S1610, one or more altered images may be generated illustrating regions of the one or more images associated with the one or more individual clinical factors correlated with the outputs of the multilayer nodes.

Embodiments of step S1610 may include then identifying which of the multilayer node outputs are most correlated with each clinical factor. The multilayer node outputs for the one or more images used for prediction relative may then be compared to the multilayer node outputs for the one or more images correlated with individual clinical factors. Each pixel or voxel in the one or more images used for prediction may then be designated as significant to the one or more individual clinical factors if the multilayer node outputs associated with the pixel or voxel are correlated with the individual clinical factors and are comparable to the multilayer node outputs found in the one or more images correlated with individual clinical factors. An overlay for each of the one or more individual clinical factors corresponding to the pixels or voxels designated as significant to the individual clinical factor may then be applied.

Embodiments of step S1610 may include iteratively removing one or more pixels or voxels from the one or more images to generate one or more stripped images. The previously trained deep neural network may then be applied to the one or more stripped images. One or more differences may then be identified in the outputs of the multilayer nodes for the one or more stripped images relative to the outputs of the multilayer nodes for the one or more images. The one or more differences may then be compared to the previously identified patterns of node outputs for the plurality of individual clinical factors. In embodiments where the differences are correlated with the previously identified patterns of node outputs for the plurality of individual clinical factors, a pixel or voxel may then be designated as associated with the one or more individual clinical factors correlated with the outputs of the multilayer nodes. An overlay corresponding to the pixels or voxels designated as associated with the one or more individual clinical factors may then be applied.

Figure 15:
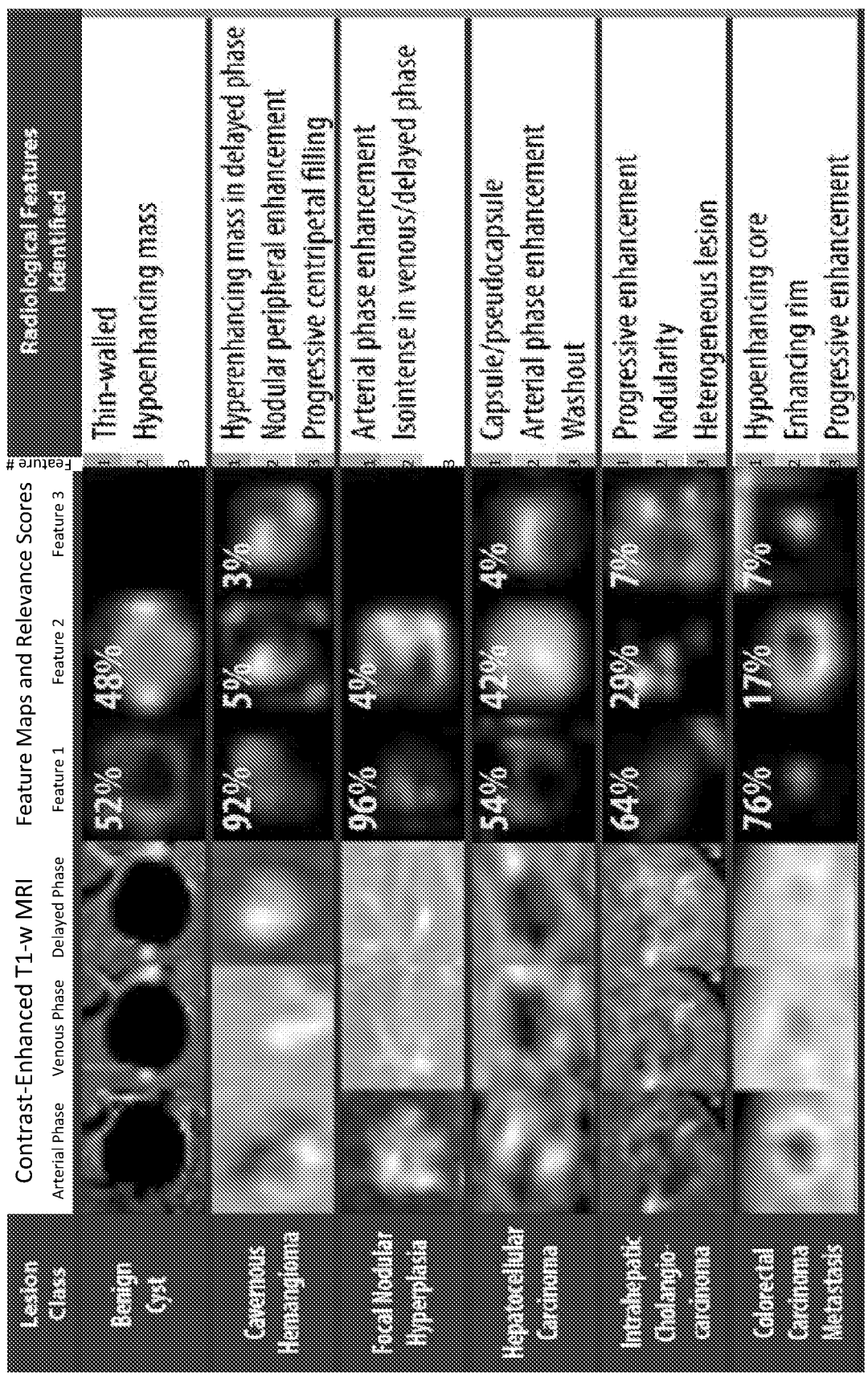
FIG. 15 depicts feature maps and relevance scores for examples of lesions from each class with correctly identified features. The color and ordering of the feature maps correspond to the ranking of the feature relevance scores, with the most relevant feature's map in red. The feature maps are created based on the entire MRI sequence, and do not correspond directly to a single phase. These results are taken from a single iteration.

Embodiments of the present invention construct an end-to-end "interpretable clinical AI" system that could drastically enhance the efficiency and accuracy of radiology and may easily integrate into a clinical workflow, providing not just accurate predictions, but also clear rationale behind these projections, as depicted in FIG. 15.

Figure 17:
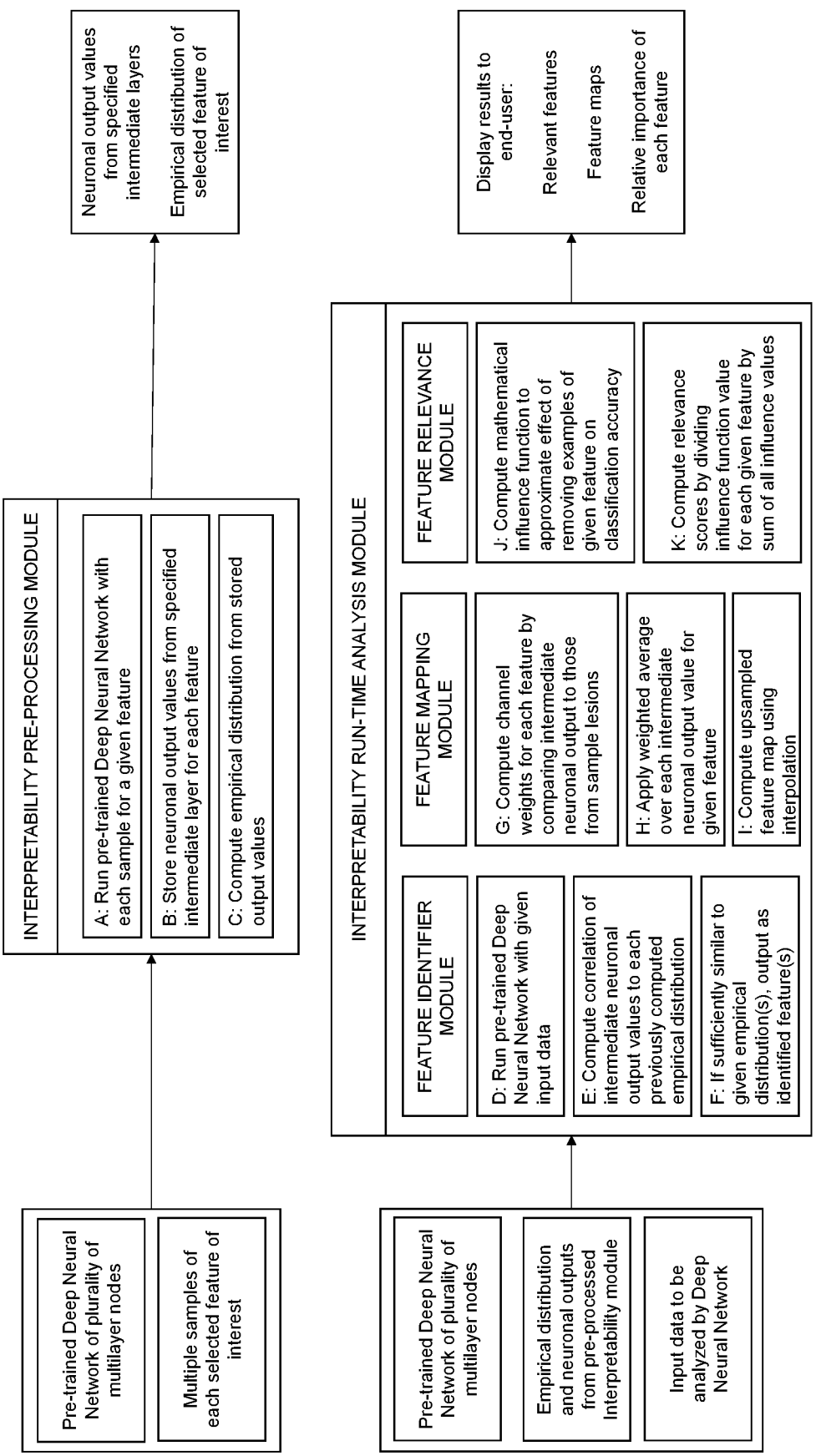
FIG. 17 depicts a system including an interpretability pre-processing module and an interpretability run-time analysis module according to an embodiment of the invention.

Referring now to FIG. 17, embodiments of the invention can further include a system including an interpretability pre-processing module and an interpretability run-time analysis module.

The interpretability pre-processing module can take inputs including a pre-trained deep neural network of plurality of multilayer nodes as well as multiple samples of each selected feature of interest and include subtasks to (A) run a pre-trained deep neural network with each sample for a given feature, (B) store neuronal output values from specified intermediate layer for each feature, and (C) compute empirical distribution from stored output values. This module can produce an output including neuronal output values from specified intermediate layers and the empirical distribution of at least one selected feature of interest.

The interpretability run-time analysis module can take inputs including pre-trained deep neural network of plurality of multilayer nodes, empirical distribution and neuronal outputs from pre-processed interpretability module, and input data to be analyzed by deep neural network. The run-time analysis module can include multiple sub-modules, including a feature identifier module, a feature mapping module, and a feature relevance module, as described below.

The computer-implemented method can include a module for identifying features. The feature identifier module can further include subtasks, including: (D) running a pre-trained deep neural network with given input data, (E) computing correlation of intermediate neuronal output values to each previously computed empirical distribution, and (F) computing whether neuronal outputs are sufficiently similar to at least one given empirical distribution.

The computer-implemented method can include a module for generating a contribution score for one or more of the plurality of individual clinical factors. The generating the contribution score module can further include subtasks, including: (J) computing a mathematical influence function to approximate the effect of removing specified examples of a given feature on classification accuracy; (K) computing relevance scores by dividing the value of the influence function for a given feature by the sum of all feature influence function values. Generating the contribution score module can also further include subtasks for iteratively removing one or more of the multilayer nodes associated with the previously identified patterns of node outputs for one of the plurality of individual clinical factors from the previously trained deep neural network to produce an altered deep neural network; applying the altered deep neural network to the one or more images to produce an altered prediction; and computing a difference between the altered prediction and the prediction. The generating the contribution score module can further include: quantifying the impact of removing the multilayer nodes associated with the previously identified patterns of node outputs for one of the plurality of individual clinical factors. The generating the contribution score module can further include: quantifying the impact of removing one or more images having a single clinical factor on the prediction of the deep neural network.

The computer-implemented method can further include modules for generating one or more altered images illustrating regions of the one or more images associated with the one or more individual clinical factors correlated with the outputs of the multilayer nodes. The generating one or more altered images module can further include: (G) computing channel weights for each feature by comparing intermediate neuronal output to those from sample lesions, (H) applying weighted average over each intermediate neuronal output value for given feature, and (I) computing an upsampled feature map using interpolation. The generating one or more altered images module can further include: identifying which of the multilayer node outputs are most correlated with each clinical factor; comparing the multilayer node outputs for the one or more images used for prediction relative to the multilayer node outputs for the one or more images correlated with individual clinical factors; designating each pixel or voxel in the one or more images used for prediction as significant to the one or more individual clinical factors if the multilayer node outputs associated with the pixel or voxel are correlated with the individual clinical factors and are comparable to the multilayer node outputs found in the one or more images correlated with individual clinical factors; and applying an overlay for each of the one or more individual clinical factors corresponding to the pixels or voxels designated as significant to the individual clinical factor. The generating one or more altered images method can further include: iteratively removing one or more pixels or voxels from the one or more images to generate one or more stripped images; reapplying the previously trained deep neural network to the one or more stripped images; identifying one or more differences in outputs of the multilayer nodes for the one or more stripped images relative to the outputs of the multilayer nodes for the one or more images; comparing the one or more differences to the previously identified patterns of node outputs for the plurality of individual clinical factors; designating a pixel or voxel as associated with the one or more individual clinical factors correlated with the outputs of the multilayer nodes if the differences are correlated with the previously identified patterns of node outputs for the plurality of individual clinical factors; and applying an overlay corresponding to the pixels or voxels designated as associated with the one or more individual clinical factors.

The computer-implemented method can further provide a user interface comprised of a combination of the relevant clinical features, the corresponding feature maps, and the relative importance of each feature. This information can be displayed in graphical form to the user or in text form, such as a clinical report, which is auto-populated with this information as output of the previously described modules.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations that become evident as a result of the teaching provided herein.

Example 1: Deep Learning for Liver Tumor Diagnosis Development of a Convolutional Neural Network Classifier for Multi-Phasic MRI Liver cancer is the second leading cause of cancer-related deaths worldwide and hepatocellular carcinoma (HCC) represents the most common primary liver cancer. Contrary to many other cancer types, HCC incidence rates continue to rise. Rapid and reliable detection and diagnosis of HCC may allow for earlier treatment onset and better outcomes for these patients. As the availability and quality of cross-sectional imaging have improved, the need for invasive diagnostic biopsies has decreased, propelling imaging-based diagnosis to a more central role, with a unique status especially for primary liver cancer. However, the radiological diagnosis of potentially malignant hepatic lesions remains a challenging task. In this setting, standardized image analysis and reporting frameworks such as the Liver Imaging Reporting and Data System (LI-RADS) can improve radiological diagnosis by reducing imaging interpretation variability, improving communication with referring physicians, and facilitating quality assurance and research. However, the increasing complexity of LI-RADS has made its implementation less feasible in a high-volume practice, leaving an unmet clinical need for computational decision-support tools to improve workflow efficiency.

Machine learning algorithms have achieved excellent performance in the radiological classification of various diseases and may potentially address this gap. In particular, a deep learning system (DLS) based on convolutional neural networks (CNNs) can attain such capabilities after being shown imaging examples with and without the disease. Unlike other machine learning methods, CNNs do not require definition of specific radiological features to learn how to interpret images, and they may even discover additional differential features not yet identified in current radiological practice.

However, such capabilities have not yet been fully demonstrated in the realm of HCC imaging. Most prior machine learning studies classified liver lesions on two-dimensional (2D) CT slices and ultrasound images. However, higher performance may be achieved with a model that analyzes 3D volumes of multi-phasic contrast-enhanced MRI, which is the reference standard for image-based diagnosis.

Therefore, this study is aimed to develop a preliminary CNN-based DLS that demonstrates proof-of-concept for classifying six common types of hepatic lesions with typical imaging appearances on contrast-enhanced MRI, and to validate performance with comparison to experienced board-certified radiologists.

Materials and Methods

Figure 2:
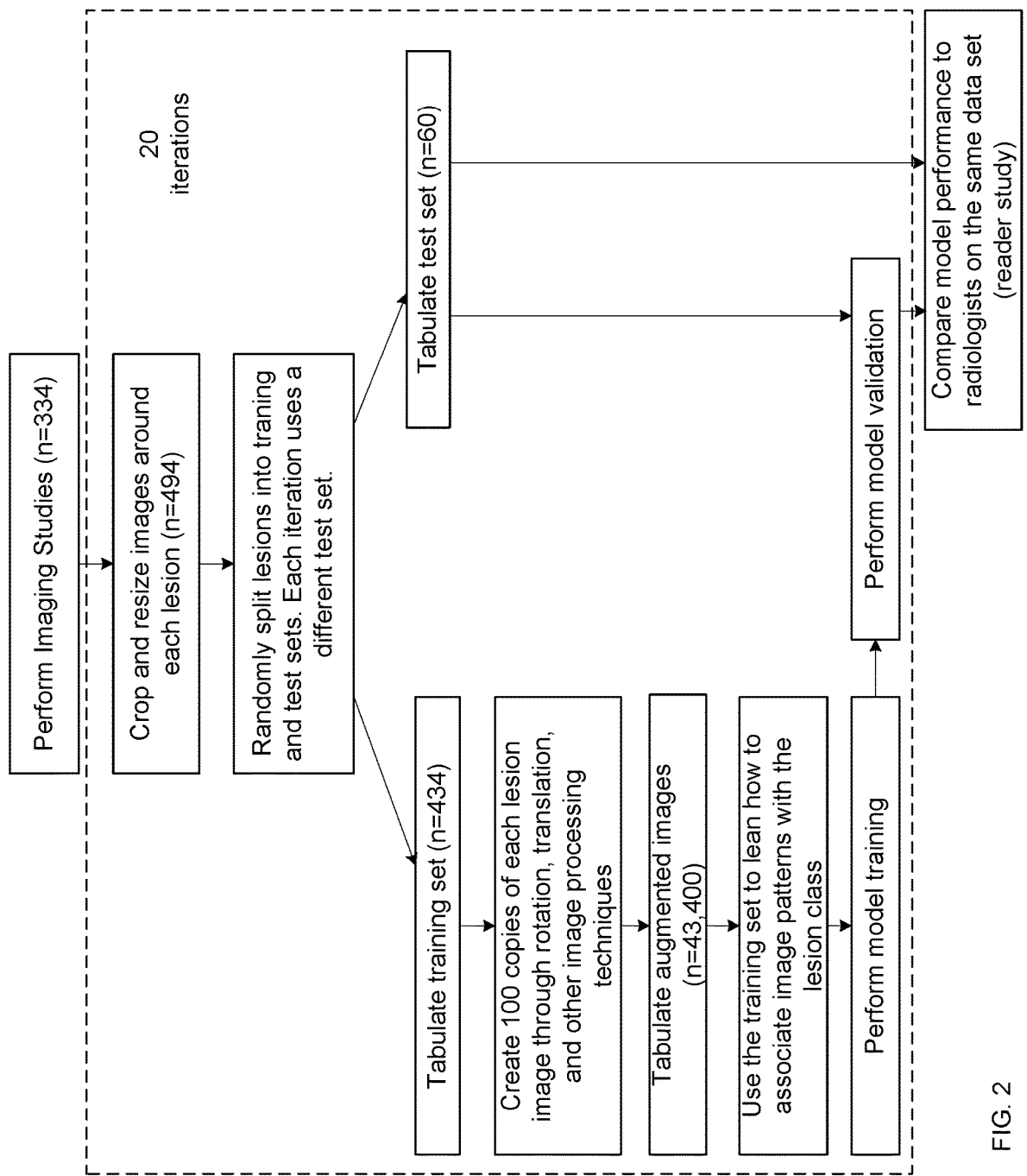
FIG. 2 depicts a flowchart of an exemplary lesion classification approach of the present invention, including model training, model testing and a reader validation study.

This was a single-center engineering development and validation study compliant with the Health Insurance Portability and Accountability Act and the Standards for Reporting of Diagnostic Accuracy guidelines. The study was approved by the institutional review board and informed consent was waived. The two components of the study involved (1) engineering a CNN-based liver tumor classifier, followed by (2) proof-of-concept validation of the final optimized CNN by comparison with board-certified radiologists on an identical unseen dataset. An overview of the model training and validation portions is illustrated in FIG. 2.

Establishment of Ground Truth Cases

A medical student (CH) searched the picture archiving and communication system (PACS) for abdominal MRI examinations between 2010 and 2017 depicting one of the following hepatic lesions: simple cyst, cavernous hemangioma, focal nodular hyperplasia (FNH), HCC, intrahepatic cholangiocarcinoma (ICC) and colorectal cancer (CRC) metastasis. Due to the nature of a single-institution investigation with limited availability of pathologic proof, lesions were restricted to those displaying typical imaging features, incorporating clinical criteria to maximize the certainty of definite diagnosis. Table 1 contains the selected criteria for the ground truth utilized for each lesion type. Diagnosed lesions formally described by radiology faculty on official reports were double-checked post hoc according to these criteria with another radiological reader (BL), and lesions were excluded if they contained discrepancies or displayed poor image quality. Up to three imaging studies per patient were included as long as studies were more than three months apart. Up to nine different lesions were used in each study. The majority of included lesions were untreated; treated lesions were only included if the selected lesion showed progression or the patient underwent loco-regional therapy more than one year ago and now presented with residual tumor. Patients younger than 18 years were excluded.

TABLE 1

| | Reference Standard for included lesions. | |
|---|---|---|
| Lesion Type | Imaging Characteristics | Non-imaging criteria |
| Cyst | Sharply defined, thin walled lesion with no septations or signs of hemorrhage or inflammation Hypointense and no enhancement of content on contrast enhanced phases | Diagnosed solely based on imaging characteristics |
| Cavernous Hemangioma | Well-circumscribed, spherical to ovoid mass Early peripheral, nodular or globular, discontinuous enhancement on arterial phase Progressive centripetal enhancement with isointensity to blood vessels on portal venous phase Persistent filling or completely filled hyperintense | Diagnosed solely based on imaging characteristics |

TABLE 1-continued

Reference Standard for included lesions.

| Lesion Type | Imaging Characteristics | Non-imaging criteria |
| --- | --- | --- |
| | mass on delayed phase "Flash-filling" lesions were not included in this study. | |
| Focal Nodular Hyperplasia | Round shaped focal liver mass with homogenous enhancement and marked hyperintensity in the arterial phase Lesion blends into the surrounding parenchyma as it becomes isointense on portal venous and delayed phase the Potential central/stellate scar shows uptake enhancement and is hyperintense on portal venous and delayed phases Presence of a central scar was not necessary for being classified as classic appearing, as the definition of assuming the presence of a stellate scar as a typical feature is generally discussed in literature | Diagnosed solely based on imaging characteristics |
| Hepatocellular carcinoma | OPTN5A: Size: 1-2 cm Representing all of the following features: Increased contrast enhancement on arterial phase Washout during portal venous or delayed phases Peripheral rim enhancement, illustrating a capsule or pseudocapsule OPTN5B: Size: 2-5 cm Arterially hyperenhancing and has at least one of two venous features: Washout Peripheral rim enhancement OPTN5X: Size: >5 cm Arterially hyperenhancing and has at least one of two venous features: Washout Peripheral rim enhancement | Only lesions which were classified as OPTN 5A, OPTN 5B or OPTN5X HCCs were included. The classification criteria for HCC in the UNOS/OPTN system were developed in such way HCC can be unequivocally diagnosed by using imaging. The diagnostic imaging criteria driving HCC classification rely on the characteristic appearance of HCC on dynamic multiphasic contrast-enhanced CT scans or MR images. OPTN class 5 indicates that a nodule meets radiologic criteria for HCC. |
| Intrahepatic cholangiocarcinoma | Either well circumscribed, large with lobulated margins or masses with an infiltrative growth pattern Delayed enhancement with a progressive and concentric filling pattern on contrast enhanced phases Distally adjacent bile ducts may show prominent enlargement | Histopathologic report from biopsy or surgery Clinical information and therapy approach |
| Colorectal carcinoma metastases | Well-circumscribed, spherical to ovoid mass Typical enhancement pattern of hypovascular metastases with a hypointense center and peripheral enhancement; "target" lesion appearance Potential perilesional enhancement due to tumor vascularity or hepatic edema Over time the central part of the lesion remains hypointense due to necrosis or hypovascularity | Histopathologic report from biopsy or surgery Clinical information and therapy approach Known history of primary malignancy |

MRI Acquisition Protocol

This study involved MRI examinations performed from 2010 to 2017 available throughout the institutional PACS, designed to include a heterogeneous collection of MRI scanners and imaging studies. This incorporated both 1.5-T and 3-T MR scanners, including Siemens Aera, Espree, Verio, Avanto, Skyra, and Trio Tim and GE Discovery and Signa Excite scanners. Multi-phasic contrast-enhanced. T1-weighted breath-hold sequences from standard institutional liver MR imaging protocols were used with acquisition times of 12-18 seconds. Several different gadolinium-based agents were used (dosed at 0.1 mmol/kg), including Dotarem (Guerbet), Gadavist (Bayer), Magnevist (Bayer), ProHance (Bracco Diagnostics), and Optimark (Covidien).

Post-contrast: images were analyzed, including late arterial phase (about 20 seconds post-injection), portal venous phase (about 70 seconds post-injection) and delayed venouse phase (about 3 min post-injection). Imaging parameters varied across different scanners and time frames; however, the majority were in the range of TR 3-5 ms, TE 1-2 ms, flip angle 9-13°, bandwidth 300-500 Hz, slice thickness 3-4 mm, image matrix 256×132 to 320×216, and field-of-view 300× 200 mm to 500×400 mm.

Image Processing

Eligible MRI studies were downloaded from the PACS and stored as DICOM files. The location and size of a 3D bounding box around the target lesion were manually recorded on the on the x-, y-, and z-axis.

Figure 7:
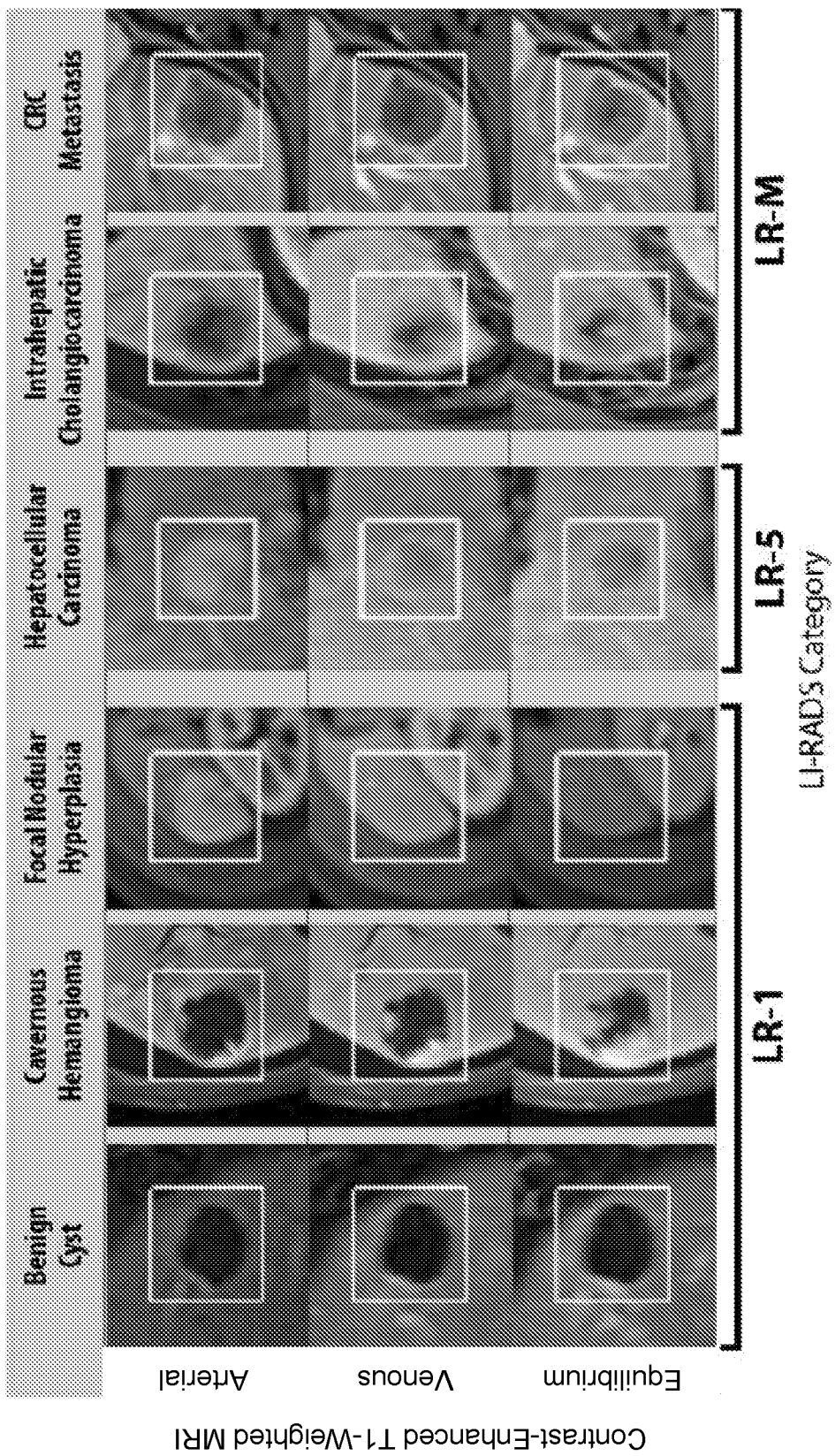
FIG. 7 depicts exemplary images of lesion classes and corresponding LI-RADS categories. Boxes indicate the cropping of each lesion, which adds padding to the lesion coordinates as determined by a radiologist. The model was able to overcome extrahepatic tissues such as the kidney.

The images were processed and automatically cropped to show only the lesion of interest using code written in the programming language Python 3.5 (Python Software Foundation, Beaverton, Oregon, USA). The cropped image was then resampled to a resolution of 24×24×12 voxels (FIG. 7). To minimize bias field effects, cropped images were normalized to intensity levels from −1 to 1. Affine registration with a mutual information metric was used to register portal venous and delayed phase.

MRI Studies to the Arterial Phase

Ten lesions from each class were randomly selected to comprise the test set (12% of the entire dataset) using Monte Carlo cross-validation and the remaining lesions comprised the training set. Each image in the training set was augmented by a factor of 100 using established techniques to increase the number of training samples, which allows the model to learn imaging features that are invariant to rotation or translation. During augmentation, images randomly underwent rotation, translation, scaling, flipping, interphase translation, intensity scaling, and intensity shifting.

Deep Learning Model Development

Figure 3:
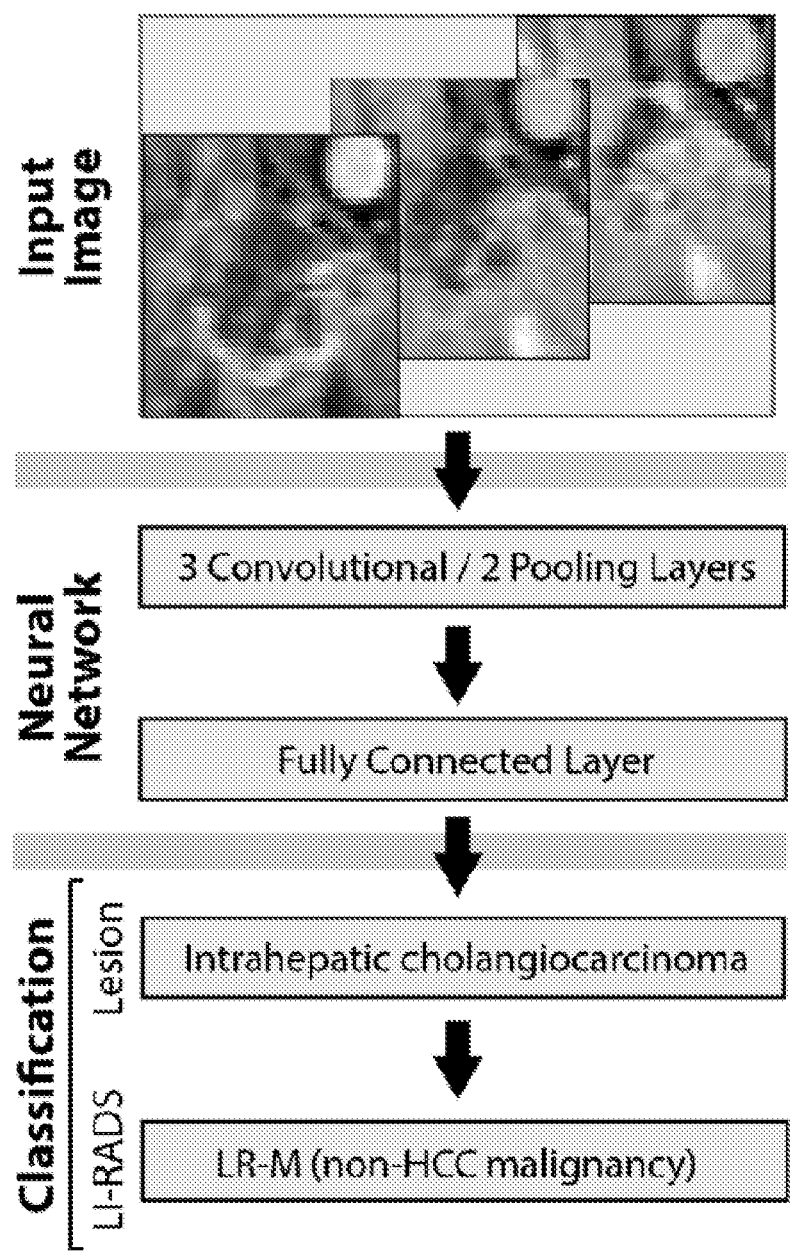
FIG. 3 depicts an exemplary neural network model architecture used to infer the lesion entity based on an input image, shown for an example of intrahepatic cholangiocarcinoma. The Liver Imaging Reporting and Data System (LI-RADS) classification follows from the lesion class.

The CNN model was trained on a GeForce GTX 1060 (NVIDIA, Santa Clara, California, USA) graphics processing unit. The model was built using Python 3.5 and Keras 2.2 (https://keras.io/) running on a Tensorflow backend (Google, Mountain View, California, USA, https://www.tensorflow.org/). Model engineering consisted of iteratively adjusting the network architecture (number of convolutional layers, pooling layers, fully connected layers, and filters for each layer, along with parameter optimization) and training cases (removing cases with poor imaging quality or ambiguous imaging features and increasing the number of training samples for lesion classes demonstrating lower performance). The final CNN consisted of three convolutional layers, where the first layer had 64 convolutional filters for each of the three phases in the original image, and the other two had 128 filters across all phases. Each filter generated filtered images by convolving voxels in 3×3×2 blocks. The model also contained two maximum pooling layers (size 2×2×2 and 2×2×1 respectively), which reduce the resolution of filtered images to provide spatial invariance (i.e. a feature that is shifted by a voxel can still be represented by the same neuron, which facilitates learning). The final CNN contained two fully connected layers, one with 100 neurons and the second with a softmax output to six categories that corresponded to the lesion types (FIG. 3). The selected imaging studies spanned 296 patients (155 male/141 female) (Table 1). A total of 334 imaging studies were selected, with a combined total of 494 lesions (74 cysts, 82 cavernous hemangiomas, 84 FNHs, 109 HCCs, 58 ICCs, 87 CRC metastases). The average diameter of all lesions used was 27.5±15.9 mm, ranging from 21.7±15.5 mm for simple cysts to 45±16.8 mm for ICCs (Table 2). The CNN used rectified linear units after each convolutional layer and the first fully connected layer, which helps the model to learn non-linear features. These are used in conjunction with batch normalization and dropout, which are regularization techniques that help the model to generalize beyond the training data. Each CNN was trained with an Adam optimizer using minibatches of five samples from each lesion class. Hyperparameters were chosen via an exhaustive search through a manually specified portion of the search, an approach known in the literature as a grid search. Samples were chosen randomly from the augmented dataset. The model was then tested on its ability to correctly classify the 60 lesions in the test dataset (10 from each lesion class) and performance was averaged over 20 independent training iterations with different groupings of training and test datasets to gain a more accurate assessment.

Reader Study Validation

After development of between the CNN model was complete, the classification accuracy of the final CNN was compared with two board-certified radiologists, using an identical set of randomly selected lesions that were unseen by either the CNN model or the radiologists. The two radiologists (39 and 7 years of experience, did not take part in the model training process and were blinded to the lesion selection. The reader study was conducted on an OsiriX MD (v.9.0.1, Pixmeo SARL, Switzerland, Geneva) workstation. To provide even comparison of input data available to the CNN model, the simulated ready study contained several differences compared to actual clinical practice. The imaging studies were anonymized, and the radiologists were fully blinded to clinical data as well as MRI sequences not utilized for the CNN training. The test set for the reader study consisted of 10 randomly selected lesions of each class, 60 lesions in total, while the remaining lesions were assigned to the training set. The randomization was based on Monte Carlo cross-validation and the results of the reader study were com-pared after a single iteration to mimic their first exposure to the images. Each radiologist independently classified the 60 lesions characterized by the model in the test set based on the original three contrast-enhanced MRI phases (late arterial, portal venous and delayed/equilibrium). Their performance was evaluated in distinguishing the six lesion entities as well as three broader categories that simulate the application of a deep learning model to an HCC diagnostic imaging framework such as LI-RADS. The three broader derived categories were HCCs (corresponding to LR-5), benign lesions (grouping cysts, hemangiomas and FNHs, corresponding to LR-1), and malignant non-HCC lesions (grouping ICCs and CRC metastases, corresponding to LR-M). The radiologists did not scroll any further than the superior and inferior margins of the lesion in order to avoid revealing possible other lesions within the liver and thereby biasing the read. The time from opening the MRI phases until classification of the lesion was recorded.

Statistics

The performance of the model was evaluated by averaging the sensitivity, specificity, and overall accuracy over 20 iterations, as described above. For validation of the CNN with radiological readings, the performances of both the model and the radiologists were computed by evaluating sensitivity, specificity, and overall accuracy on the same single randomly selected test set of unseen cases. Prevalence-based parameters such as positive predictive value and negative predictive value were not applicable for this study. A receiver operating characteristic curve was plotted to compare the model and radiologist performance in identifying HCC masses.

Results

Study Cohort Selection

The selected imaging studies spanned 296 patients (155 male/141 female). The mean age of the patients at imaging was 57±13.6 years (standard deviation). A total of 334 imaging studies acquired between 2010 to 2017 were selected, with a combined total of 494 lesions (74 cysts, 82 cavernous hemangiomas, 84 FNHs, 109 HCCs, 58 ICCs, 87 CRC metastases). The average diameter of all lesions used was 27.5±15.9 mm, ranging from 21.7±15.5 mm for simple cysts to 45±16.8 mm for ICCs (Table 2).

TABLE 2

Patient characteristics and demographics. Total column does not equal the sum of the rows because some patients had multiple lesion types

| Patient Characteristics | Cyst | Cavernous Hemangioma | FNH | HCC | ICC | CRC metastasis | Total |
|---|---|---|---|---|---|---|---|
| Number of Patients | 37 | 49 | 53 | 88 | 36 | 39 | 296 |
| Age at imaging (mean ± SD | 62 ± 10 | 50 ± 11 | 43 ± 11 | 63 ± 8 | 63 ± 14 | 61 ± 14 | 57 ± 14 |
| Gender | | | | | | | |
| Male | 19 | 17 | 8 | 67 | 18 | 27 | 155 |
| Female | 18 | 32 | 45 | 21 | 18 | 12 | 141 |
| Ethnicity | | | | | | | |
| Caucasian | 29 | 39 | 34 | 50 | 25 | 32 | 206 |
| African American | 2 | 3 | 11 | 12 | 3 | 2 | 32 |
| Asian | 3 | 0 | 0 | 3 | 1 | 0 | 5 |
| Other | 0 | 3 | 2 | 12 | 3 | 4 | 24 |
| Unknown | 3 | 4 | 6 | 11 | 4 | 1 | 29 |

Deep Learning Model

The final CNN demonstrated a training accuracy of 98.7%±1.0 (8567/8680 volumetric samples) across six lesion types and 99.1%±0.7 (8602/8680) according to the three general derived LI-RADS categories (Table 3). The average test accuracy was 91.9%±2.9 (1103/1200) among individual lesions and 94.3%±2.9 (1131/1200) across the three broader categories. The time to initially train the DLS was 29 minutes±4 minutes. Once the model was trained, the actual run-time to classify each lesion in the test data set was 5.6 milliseconds±6 milliseconds.

TABLE 3

Imaging details for each category of lesion. Total column does not equal the sum of the rows because some imaging studies had multiple lesion types.

| Image Characteristics | Cyst | Cavernous Hemangioma | FNH | HCC | ICC | CRC metastasis | Total |
|---|---|---|---|---|---|---|---|
| Number of Patients | 37 | 49 | 53 | 88 | 36 | 39 | 296 |
| Number of Imaging Studies | 42 | 50 | 57 | 96 | 49 | 44 | 334 |
| Number of Lesions | 74 | 82 | 84 | 109 | 58 | 87 | 494 |
| Lesion Diameter (mm, mean ± SD) | 21.7 ± 15.5 | 25 ± 11.6 | 28.4 ± 20.7 | 24.4 ± 10 | 45 ± 16.8 | 26.4 ± 12.3 | 27.5 ± 15.9 |

For the 20 iterations, the average model sensitivity across the six lesion types was 92%, with an average specificity of 98% (Table 4). The model sensitivity for individual lesion types ranged from 89% (177/200) for CRC metastases to 99% (197/200) for simple cysts (Table 5). The corresponding model specificity for individual lesions ranged from 97% (965/1000) for ICC to 100% (1000/1000) for simple cysts. HCC lesions demonstrated a sensitivity of 94% (187/200) and specificity of 98% (984/1000). For the case of the three broader categories, the sensitivity ranged from 94% (187/200 for HCC, 563/600 for benign lesions) to 95% (381/400 for malignant non-HCC lesions). The corresponding specificity ranged from 96% (770/800 for malignant non-HCC lesions, and 577/600 for benign lesions) to 98% (984/1000 for HCC). The study was conducted using the same number of lesions from each class, and thus does not reflect the actual prevalence of each lesion type.

TABLE 4

Overall accuracy and runtimes for model classification and classification by two radiologists

|  | Accuracy of Lesion Classification (mean ± SD %) | Accuracy of LI-RADS Classification (mean ± SD %) | Runtime (mean ± SD) |
|---|---|---|---|
| Average of 20 iterations | | | |
| Model Training Set | 98.7 ± 1.0 | 99.1 ± 0.7 | 29 min ± 0.4 |
| Model Test Set | 91.9 ± 2.9 | 94.3 ± 2.9 | 5.6 ms ± 4.6 |
| Reader Study (n = 60) | | | |
| Model | 90.0 | 91.7 | 1.0 ms ± 0.4 |
| Radiologist 1 | 80.0 | 88.3 | 14 s ± 10 |
| Radiologist 2 | 85.0 | 88.3 | 17 s ± 24 |

TABLE 5

Model and radiologist performance metrics for individual lesion types and LI-RADS classes ("Sens." = sensitivity; "Spec." = specificity)

|  | Average of 20 iterations | | Reader Study | | | | | |
|---|---|---|---|---|---|---|---|---|
|  | Model Test Set | | Model | | Radiologist 1 | | Radiologist 2 | |
| Lesion type | Sens. | Spec. | Sens. | Spec. | Sens. | Spec. | Sens. | Spec. |
| Cyst | 99% | 100% | 100% | 100% | 90% | 96% | 100% | 98% |
| Hemangioma | 91% | 99% | 100% | 100% | 100% | 96% | 100% | 94% |
| FNH | 91% | 89% | 90% | 96% | 90% | 98% | 90% | 94% |
| HCC | 94% | 98% | 90% | 98% | 70% | 100% | 60% | 100% |
| ICC | 90% | 97% | 60% | 100% | 80% | 94% | 90% | 100% |
| CRC metastasis | 89% | 98% | 100% | 94% | 50% | 92% | 70% | 96% |
| Overall | 92% | 98% | 90% | 98% | 80% | 96% | 85% | 97% |
| LI-RADS class | | | | | | | | |
| LR-1 (n = 30) | 94% | 96% | 97% | 93% | 97% | 87% | 100% | 80% |
| LR-5 (n = 10) | 94% | 98% | 90% | 98% | 70% | 100% | 60% | 100% |
| LR-M (n = 20) | 95% | 96% | 95% | 100% | 85% | 93% | 85% | 98% |
| Overall | 94% | 97% | 95% | 96% | 88% | 91% | 88% | 89% |

Reader Study

Classification of unseen randomly selected lesions included in the reader study demonstrated an average model accuracy of 90% (55/60 lesions). Radiologist accuracy was 80% (48/60) and 85% (51/60) on these same lesions, respectively (Table 4). The model accuracy for the three broader categories was 92% (58/60), compared with 88% (53/60) for both radiologists. The total elapsed time analyzing each lesion was 0.8 milliseconds for the classification model versus 14±10 seconds and 17±24 seconds for the radiologists.

Lesions included in the reader study showed an average CNN model sensitivity of 90%±14 (9/10) and specificity of 98%±2 (49/50) across the six lesion types. This compared to an average sensitivity of 80%±16 (8/10) and 85%±15 (8.5/10) and specificity of 96%±3 (48/50) 97%±3 (48.5/50) for the two radiologists respectively. The model sensitivity ranged from 70% (7/10 for FNH) to 100% (10/10 for simple cysts and hemangiomas) with a specificity ranging from 92% (46/50 for HCC) to 100% (50/50 for simple cysts, hemangiomas and ICC). Radiologist sensitivity ranged from 50% (5/10 for CRC metastases) to 100% (10/10 for simple cysts, hemangiomas), with specificity ranging from 92% (46/50 for CRC metastases) to 100% (50/50 for HCC and ICC). The average model sensitivity for three broader categories was 92% with a specificity of 97%. This compared to the radiologists' sensitivity of 88% and specificity of 89% and 91%, respectively. The model demonstrated highest sensitivity for malignant non-HCC lesions at 95% (19/20) compared to 85% (17/20) for both radiologists, whereas radiologists attained highest sensitivity for benign lesions at 97% (29/30) and 100% (30/30), compared to 90% (27/30) for the CNN.

Figure 4:
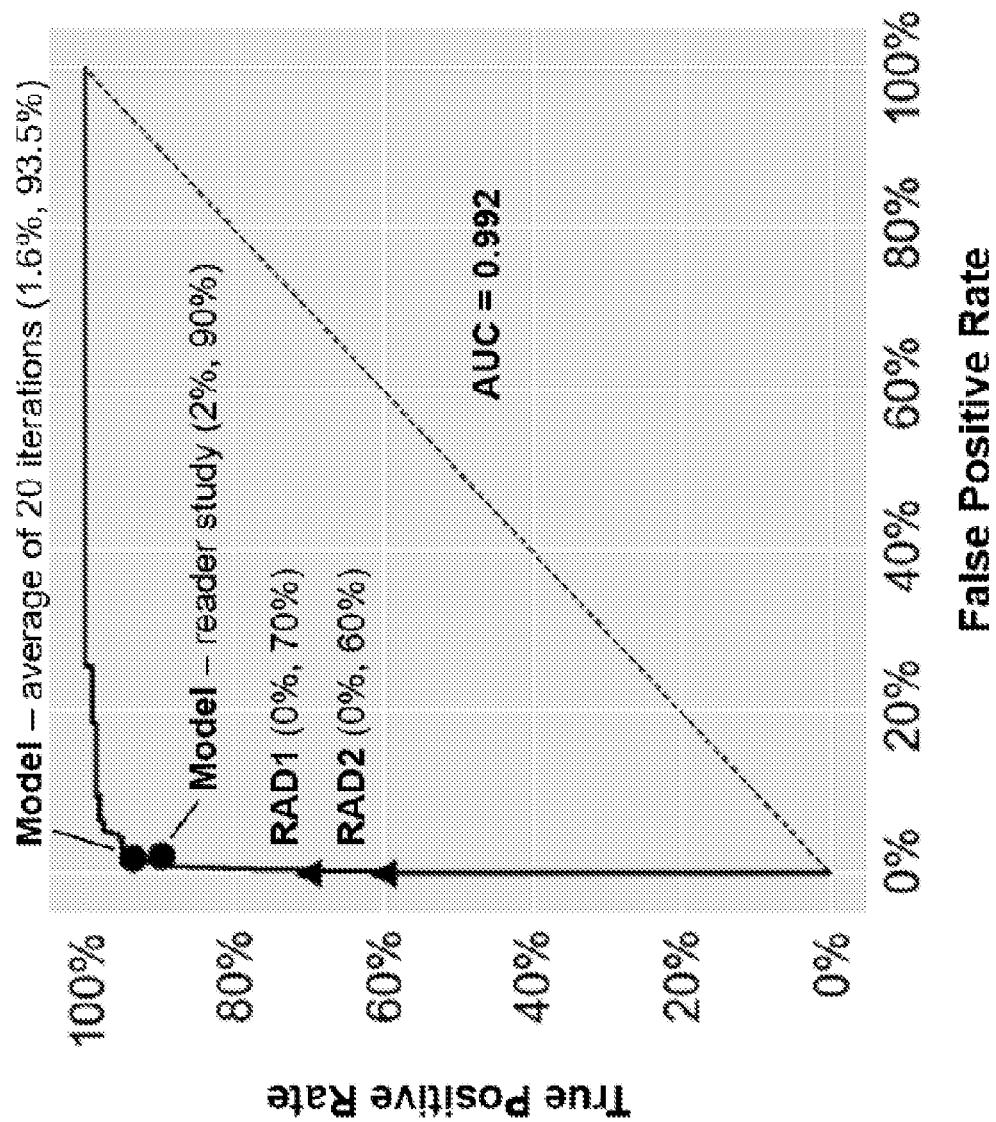
FIG. 4 depicts a model receiver operating characteristic curve for distinguishing hepatocellular carcinomas (HCCs). The model of the present invention achieves high sensitivity for HCC at the cost of a few false positives. AUC=area under curve.
Figure 5:
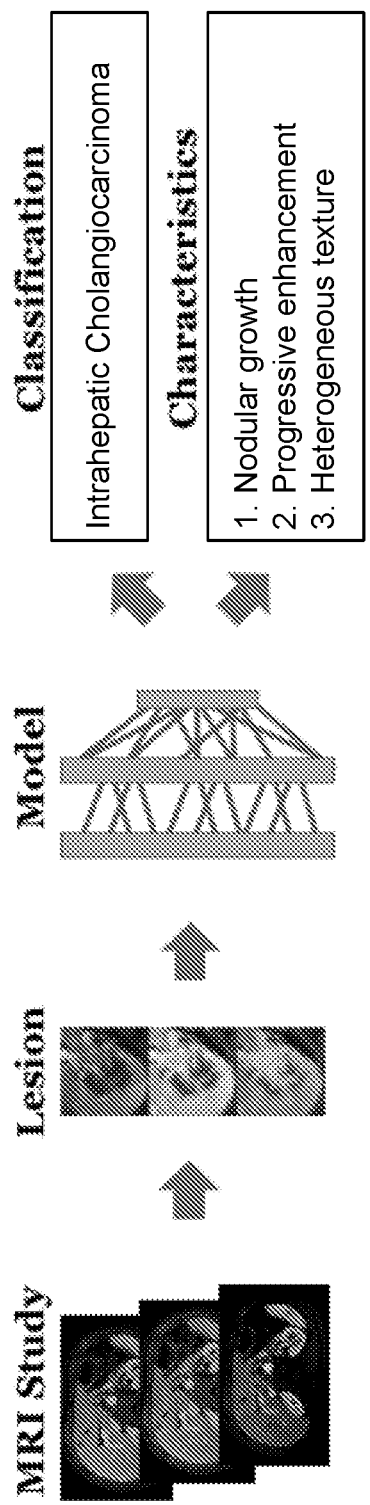
FIG. 5 depicts an exemplary process for classifying a radiological lesion with a neural network, with the addition of an interpretable AI approach that provides justifications for predictions.

A receiver operating characteristic curve was constructed by varying the probability threshold at which the CNN would classify a lesion as HCC, with an area under the curve of 0.992 (FIG. 4). This included a true positive rate of 93.5% (187/200) averaged over 20 iterations and a false positive rate of 1.6% (16/1000). When including only lesions within the reader study, the model true positive rate was 90% (9/10), and the false positive rate was 2% (1/50). Radiologists had a true positive rate of 60% and 70% (6/10 and 7/10, respectively) and a false positive rate of 0% (0/50).

Discussion

This study demonstrates a deep learning-based prototype for classification of liver lesions with typical imaging features from multi-phasic MRI, demonstrating high diagnostic performance and time efficiency. While the study did not simulate clinical practice conditions, comparison with equivalent data input showed the potential of DL systems to eventually aid in improving radiological diagnosis of six classes of hepatic lesions (model accuracy of 92%, radiologist accuracy of 80% and 85%), as well as three broader categories of benign, HCC, and malignant non-HCC lesions (model accuracy of 94%, radiologist accuracy of 88%), with a classification time of 5.6 milliseconds per lesion.

Building upon prior 2D CT and ultrasound models, the inherent improved soft tissue contrast resolution of MRI can enable this CNN to capture a wider variety of imaging features. Additionally, the 3D volumetric may improve detection of inhomogeneous growth or enhancement patterns that may be relevant to lesion classification, while removing the model's variability and dependence on manual slice selection. Furthermore, the use of heterogeneous imaging sources demonstrated the robustness of DLS in the setting of different MRI scanners and acquisition protocols. Previous studies have paved the way for computational classification of diverse lesion types by grouping hepatic lesion entities into three to five classes. Moving towards clinical implementation, classification becomes increasingly challenging when lesions are ungrouped and single entities are differentiated. In this case, a higher number of differential features must be learned with a lower chance of guessing correctly. The present study included six ungrouped lesion classes, demonstrating a high accuracy level of 91.9%. As expected, the overall accuracy was higher with three grouped classes (94.3%). In this case, there is no penalty for mistaking slowly filling cavernous hemangiomas for cysts or for confusing nodular ICCs with CRC metastases.

Since single-center developmental efforts often suffer from limited datasets, selection of idealized cases is often necessary, making the interpretation of classification results ambiguous. The direct comparison between the DLS and two radiologists allows for better interpretation of performance and potential clinical value. High sensitivity for HCC and CRC metastases was demonstrated relative to radiologists. The radiologists tended to misclassify HCCs with faint enhancement as CRC metastases and HCCs with unclear washout as FNHs, whereas the DLS could more reliably make use of other features to correctly identify the HCCs. Similarly, radiologists misclassified CRC metastases without clear progressive enhancement with cysts, and those with heterogeneous, nodular appearances were misclassified for ICCs, whereas the computational predictions were likely more robust to the absence of these features. Still, the radiologists' diagnostic accuracy may have matched or exceeded the DLS's accuracy if given access to clinical information or additional imaging sequences. As a proof-of-concept study with limited sequences, this simulated environment provided unbiased comparison between the DLS and radiologists with the same available input data.

These performance metrics suggest that a DLS could serve as a quick and reliable "second opinion" for radiologists in the diagnosis of hepatic lesions, helping to reduce interpretation difficulty and inter-reader variability when imaging features are more ambiguous. In HCC diagnosis, most inter-reader studies demonstrated a moderate level of reliability in determining LI-RADS classes, and the rigor and complexity of LI-RADS constitutes a major barrier for broad adoption. The DLS reliably classified lesions into benign, HCC and malignant non-HCC lesions (roughly corresponding to LR-1, LR-5, and LR-M respectively) with an accuracy of 94.3%. While this is a preliminary feasibility study with many limitations, it suggests that a DLS could potentially interface with LI-RADS, for example by averaging the model and radiologist predictions to score lesions that are suspicious for HCC but lack a definite benign or malignant appearance (i.e., LR-2/3/4). Such an implementation could reduce rote manual tasks, helping to simplify LI-RADS for clinical workflow integration.

In summary, this preliminary study provides proof of principle for a DLS that classifies six hepatic lesion types on multi-phasic MRI, demonstrating high performance when validated by comparison with board-certified radiologists. As the demands of radiological practice continue to increase, a synergistic workflow that combines the experience and intuition of radiologists with the computational power of DL decision-support tools may offer higher-quality patient care in a time-efficient manner.

Example 2: Deep Learning for Liver Tumor Diagnosis Part II: Convolutional Neural Network Interpretation Using Radiologic Imaging Features Introduction Deep learning (DL) systems based on convolutional neural networks (CNNs) have shown potential to revolutionize the process of radiological diagnosis (1-3). Unlike other artificial intelligence techniques, CNNs do not need to be taught specific radiological features to learn how to interpret images. A synergistic workflow that combines the experience of radiologists and the computational power of artificial intelligence systems may substantially improve the efficiency and quality of clinical care. Example 1, as described herein, demonstrated a proof-of-concept 3D CNN for the classification of liver lesions on multi-phasic MRI. Although CNNs have demonstrated high performance in diagnostic classification tasks, their "black box" design limits their clinical adoption. Despite recent advances in interpretable machine learning, deep learning models still do not provide information about the factors used in decision-making in a manner that can be understood by radiologists and other physicians, which prevents them from incorporating their results into an informed decision-making process. The inability to explain their reasoning also leads to a lack of safeguards and accountability when they fail. DL systems that demonstrate high-accuracy results in a more transparent manner are more likely to gain clinical acceptance.

This is especially applicable when incorporating DL into standardized reporting systems such as the Liver Imaging Reporting and Data System (LI-RADS). While LI-RADS has changed the diagnostic workflow of malignant lesions and contributed to a higher quality in diagnosis and reporting, most studies have demonstrated moderate inter-observer agreement for LI-RADS categories. Recent studies also highlighted issues regarding the application of LI-RADS ancillary features, which are primarily based on a combination of biological plausibility, single-center retrospective studies and expert opinion with somewhat low level of evidence. For example, the application of such features resulted in an increased number of misclassifications and ancillary features were not seen as a useful tool for assigning definite LR classes. Moreover, the application of a number of ancillary features may be inefficient, as they affected the final diagnosis in at most 10% of cases. The American College of Radiology has called for novel systems to increase the efficiency and accuracy of LI-RADS and to make it more feasible for daily radiology practice. Interpretable DL systems could help to address this gap by automating the validation, detection and standardized reporting of diagnostic imaging features, providing a way for radiologists to efficiently interact with such tools in shared decision-making paradigm.

This study investigates an integrative interpretable DL approach for DL systems used in clinical radiology, using techniques for identifying, localizing, and scoring imaging features. In addition to developing a liver lesion classifier for multi-phasic MRI (demonstrated in Example 1), the aim was to develop a proof-of-concept interpretable system that justifies aspects of its decisions through internal analysis of relevant radiologic features.

Materials and Methods

Deep Learning System Development and Model Agnostic Interpretability

Figure 12:
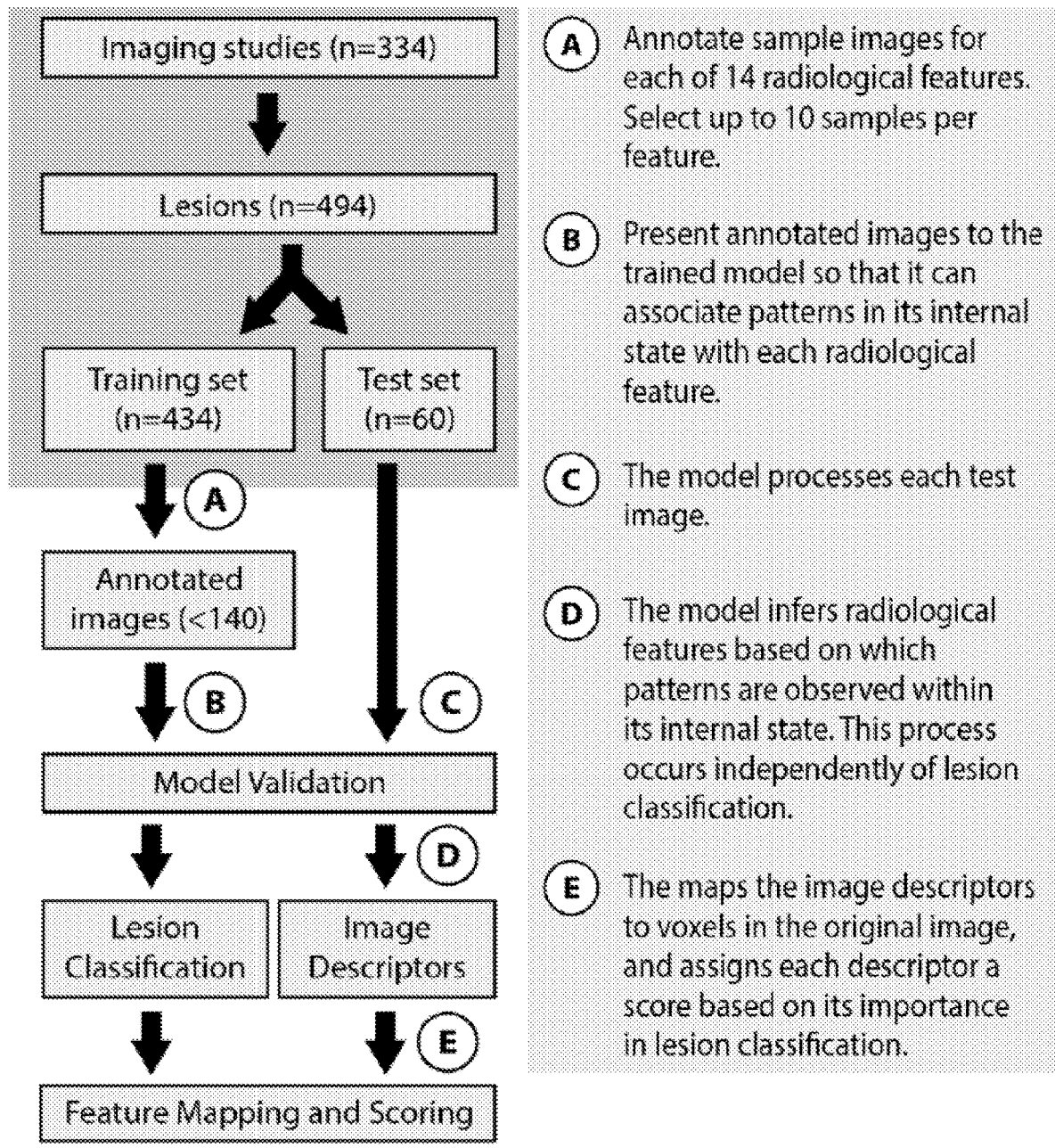
FIG. 12 depicts an exemplary flowchart of the approach for lesion classification and radiological feature identification, mapping and scoring. The entire process was repeated over 20 iterations.

This single-center retrospective study is based on an institutional review board-approved protocol and the requirement for written consent was waived. The specific methods for patient selection, lesion reference standard, MRI technique, image processing techniques and DL model are described in Example 1, herein. Briefly, a CNN was utilized with three convolutional layers and two fully connected layers, which was capable of differentiating benign cysts, cavernous hemangiomas, focal nodular hyperplasias (FNHs), HCCs, intrahepatic cholangiocarcinomas (ICCs), and colorectal carcinoma (CRC) metastases after being trained on 434 hepatic lesions from these classes. This study was integrated into the DL workflow of Example 1 so that the system could be trained to classify lesion types before incorporating techniques to identify, localize and score their radiological features (shown in FIG. 12). Specifically, the current study utilized the DL model from Part I which has been trained on a large dataset including 494 lesions. Additionally, custom algorithms were applied to analyze specific hidden layers of this pre-trained neural network in a model-agnostic approach. This method is also known as post hoc analysis (not to be confused with the post hoc analysis in statistics) and is generalizable to various pre-trained machine learning neural networks. Under the taxonomy of established interpretability methods, these algorithms fall under the general category of feature summary statistic. In terms of scope, the methods used describe local interpretability where the focus is on individual predictions, as opposed to global scope where the entire model behavior is analyzed. These selected techniques are especially useful for the purposes of communicating feature information to radiologists. These algorithms are described in detail herein.

Radiological Feature Selection

Fourteen radiological features were selected comprising lesion imaging characteristics that are observable on multi-phasic MRI and are commonly utilized in day-to-day radiological practice for differentiating between various lesion types (see Table 6). This includes LI-RADS features for HCC classification, including arterial phase hyperenhancement, washout, and pseudocapsule. Up to 20 hepatic lesions in the training set that best exemplified each feature (see examples in FIG. 13). From this sample, ten were randomly selected in each repetition of this study. Imaging features with similar appearances were grouped. A test set of 60 lesions was labeled with the most prominent imaging features in each image (1-4 features per lesion). This test set was the same as that used to conduct the reader study in Example 1.

TABLE 6

Radiological features labeled for each class. For each feature, 10 samples were randomly selected from the total set of examples.

| Radiological Features | Associated Lesion Types | Numbers of Examples |
|---|---|---|
| Arterial phase hyperenhancement | FNH, HCC | 20 |
| Central scar | FNH | 10 |
| Enhancing rim (CRC metastasis), capsule/pseudocapsule (HCC) | CRC metastasis, HCC | 20 |
| Heterogeneous lesion | ICC, HCC (OPTN5B/X) | 20 |
| Hyperenhancing mass on delayed phase | Cavernous hemangioma | 17 |
| Hypoenhancing core (CRC metastasis), Hypoenhancing mass (cyst) | Cyst, CRC metastasis | 20 |
| Infiltrate appearance | ICC | 15 |
| Isointense on venous and delayed phase | FNH | 20 |
| Nodularity | ICC | 15 |
| Nodular/discontinuous peripheral hyperenhancement | Cavernous hemangioma | 20 |
| Progressive centripetal filling | Cavernous hemangioma | 20 |
| Progressive hyperenhancement | CRC metastasis, ICC | 20 |
| Thin-walled | Cyst | 20 |
| Washout | HCC | 20 |

Feature Identification with Probabilistic Inference

Figure 14:
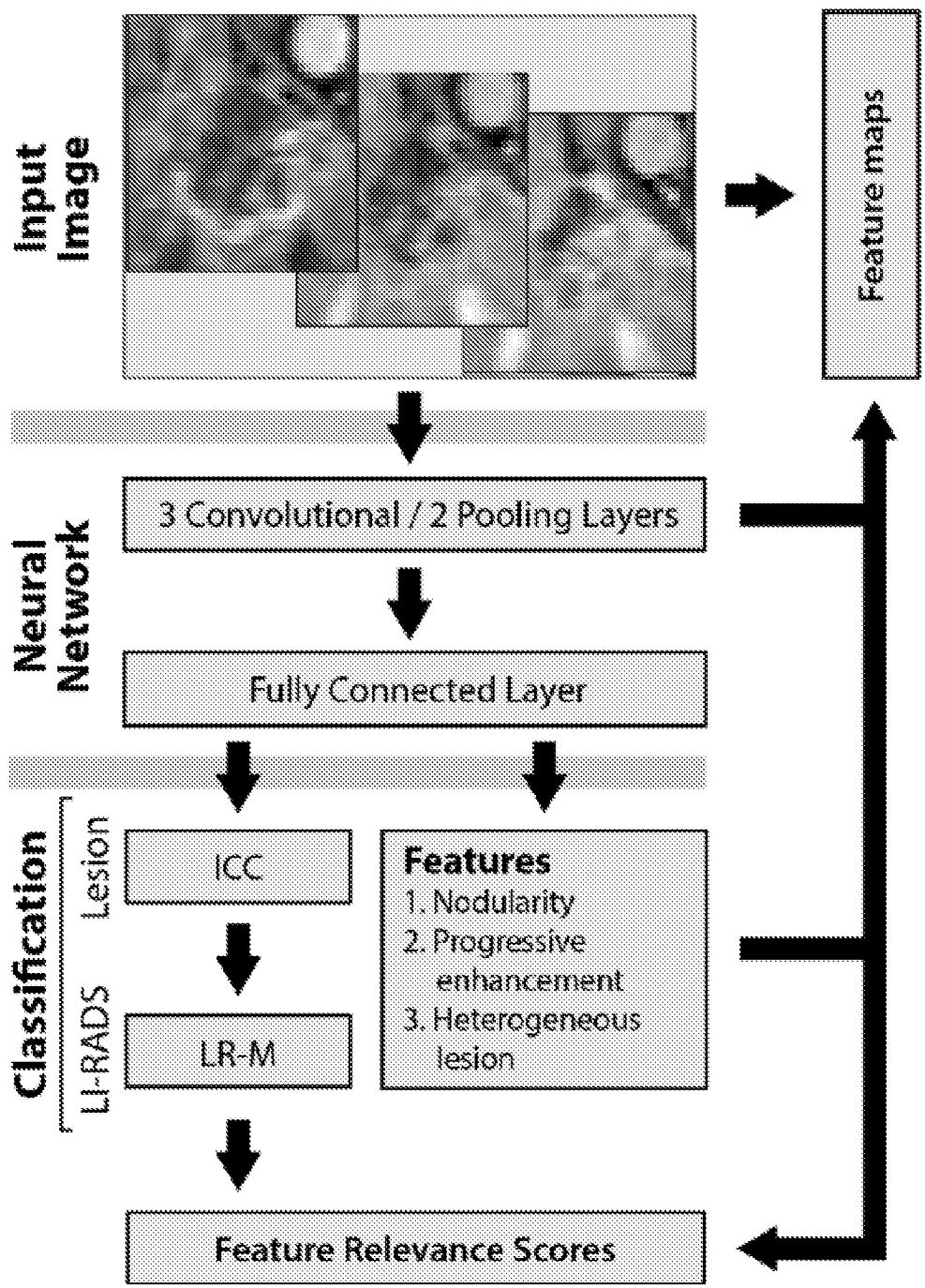
FIG. 14 depicts an exemplary CNN model architecture used to infer the lesion entity and radiological features based on the input image, shown for an example of intrahepatic cholangiocarcinoma. Patterns in the convolutional layers are mapped back to the input image to establish feature maps for each identified feature. Relevance scores are also assigned to the features based on the correspondence between patterns in the convolutional layers, the lesion classification, and the identified features.

For each radiological feature, a subset of ten sample lesions with that feature was passed through the CNN, and the intermediate outputs of the 100 neurons in the fully connected layer were inspected. By comparing these neuron outputs among the ten examples, each radiological feature was associated with specific patterns in these neurons. The test image was passed through the CNN to obtain its intermediate outputs, which were compared to the outputs associated with each feature. When the intermediate outputs of a test image are similar to the outputs observed for lesions with a particular feature, then the feature is likely to be present in the test image (shown in FIG. 14). The intermediate outputs were modeled as a 100-dimensional random variable and the training dataset was used to obtain its empirical distribution refer to marginal distributions and conditional distributions. Using kernel density estimation, the features present in each test image were probabilistically inferred. The neuronal outputs of 100 augmented versions of all images were used to provide more robust estimates of the probability distributions. As described in Example 1, image augmentation creates copies of images with stochastic distortions.

The CNN system's performance was assessed by its ability to correctly identify the radiological features in the test set of 60 labeled lesions. If it was unclear whether an imaging feature was present in a specific image, the feature was excluded from performance assessment calculations for that image. Performance was evaluated in 20 iterations with separately trained models using different choices of the ten sample lesions. Positive predictive value (PPV) and sensitivity (Sn) were measured for the entire population (averaged over the total number of features across all lesions). This was performed for each feature individually and for each lesion class.

Feature Mapping with Weighted Activations

After identifying the radiological features observed in an input lesion image, 3D feature maps were derived from the CNN's layer activations to show where features are observed within each image. For this analysis, the post-activation neuronal outputs of the final convolutional layer were used, which has 128 channels. The original images have 24×24×12 resolution and pass through padded convolutions and a 2×2×2 max pooling layer before reaching this layer at 12×12×6 spatial dimensions. The feature map was constructed for a test image by obtaining this layer's output and applying a weighted average over the 128 channels using different weights for each of the 1-4 radiological features identified within the image. The resulting 12×12×6 feature maps were upsampled using trilinear interpolation to correspond to the 24×24×12 resolution of the original image. The mapping to the three MRI phases cannot be readily traced. The channel weights used for each feature were determined by correlating the channel with at most one of the features based on the channel outputs observed in the sample lesions labeled with the feature.

Feature Scoring with Influence Functions

Among the radiological features identified in an image, some features may be more important for classifying the lesion than others. The contribution of each identified feature to the CNN's decision was analyzed by impairing the CNN's ability to learn the specific feature and examining how this impacts the quality of the CNN's classification. If the feature is not important for classifying the lesion, then the CNN should still make the correct decision, even if it can no longer identify the feature. The CNN's ability to learn a particular feature can be hampered by removing examples of that feature from its training set. Although repeatedly removing examples and retraining the model is prohibitively time-consuming, Koh et al. developed an approximation of this process that calculates an influence function. The influence function of a feature with respect to a particular image estimates how much the probability of the correct lesion classification deteriorates for that image as examples of the feature are removed from the CNN's training set. Thus, the radiological feature that is most influential for classifying a particular lesion is the feature with the largest influence function for that image. Scores were obtained for each feature by measuring their respective influence functions, then dividing each by the sum of the influences. No ground truth was used for the optimal weighting of radiological features for diagnosing a given image, since a CNN does not "reason" about radiological features in the same way as a radiologist.

Statistical Analysis

The performance of the CNN model in identifying radiological features in the image was evaluated on the test set of 60 lesions using positive predictive value (PPV) and sensitivity (Sn) for the entire population as well as for each feature individually. In addition, PPV and Sn were analyzed with respect to each lesion class. The PPV and sensitivity were averaged over the total number of features across all lesions rather than averaged individually for each lesion. The standard deviations of each were calculated with respect to the 20 iterations.

Results

Feature Identification with Probabilistic Interference

A total of 224 annotated images were used across the 14 radiological features, and some images were labeled with multiple features. After being presented with a randomly selected subset of 140 out of 224 sample lesions, the model obtained a PPV of 76.5±2.2% and Sn of 82.9±2.6% in identifying the 1-4 correct radiological features for the 60 manually labeled test lesions over 20 iterations (see Table 7).

TABLE 7

Precision and recall of the model for determining individual radiological features present in lesion images.

| Radiological Feature | Positive Predictive Value (mean ± SD) | Sensitivity (mean ± SD) |
| --- | --- | --- |
| Arterial phase hyperenhancement | 91.2 ± 5.6% | 90.3 ± 3.8% |
| Central scar | 32.0 ± 21.7% | 80.0 ± 40.0% |
| Enhancing rim (CRC metastasis), capsule/pseudocapsule (HCC) | 74.8 ± 7.5% | 75.3 ± 8.7% |
| Heterogeneous lesion | 64.9 ± 4.8% | 75.6 ± 5.4% |
| Hyperenhancing mass on delayed phase | 93.0 ± 6.2% | 100.0 ± 0.0% |
| Hypoenhancing core (CRC metastasis), Hypoenhancing mass (cyst) | 82.4 ± 4.5% | 71.3 ± 11.8% |
| Infiltrate appearance | 33.0 ± 11.3% | 45.0 ± 10.0% |
| Isointense on venous and delayed phase | 69.5 ± 8.7% | 92.2 ± 9.4% |
| Nodularity | 62.9 ± 14.0% | 60.8 ± 22.5% |
| Nodular/discontinuous peripheral hyperenhancement | 80.3 ± 10.0% | 94.0 ± 7.3% |
| Progressive centripetal filling | 73.7 ± 8.5% | 95.0 ± 5.5% |
| Progressive hyperenhancement | 87.1 ± 5.4% | 92.6 ± 3.9% |
| Thin-walled | 86.5 ± 8.5% | 100.0 ± 0.0% |
| Washout | 67.4 ± 10.0% | 66.7 ± 9.3% |
| Overall | 76.5 ± 2.2% | 82.9 ± 2.6% |

Among individual features, the model was most successful at identifying relatively simple enhancement patterns. With a mean number of 2.6 labeled features per lesion the model achieved a precision of 76.5±2.2% with a recall of 82.9±2.6% (see Table 8). It achieved the best performance at identifying arterial phase hyper-enhancement (PPV=91.2%, Sn=90.3%), hyperenhancing mass on delayed phase (PPV=93.0%, Sn=100%), and thin-walled mass (PPV=86.5%, Sn=100%). In contrast, the model performed relatively poorly on more complex features, struggling to identify nodularity (PPV=62.9%, Sn=60.8%) and infiltrative appearance (PPV=33.0%, Sn=45.0%). The CNN also overestimated the frequency of central scars (PPV=32.0%, Sn=80.0%), which only appeared once among the 60 test lesions.

TABLE 8

Precision and recall of the model for determining the radiological features present in images grouped by lesion class.

| Lesion Class | Feature 1 | Feature 2 | Feature 3 | Feature 4 |
|---|---|---|---|---|
| Benign cyst | Thin-walled (67.1%) | Hypoenhancing mass (46.6%) | N/A | N/A |
| Cavernous hemangioma | Progressive centripetal filling (48.6%) | Hyperenhancing mass on delayed phase (34.0%) | Nodular/discontinuous peripheral hyperenhancement (21.6%) | N/A |
| Focal nodular hyperplasia | Isointense on venous/delayed phase (79.4%) | Arterial phase hyperenhancement (65.8%) | Central scar (37.4%) | N/A |
| Hepatocellular carcinoma | Capsule/pseudocapsule (49.5%) | Heterogeneous lesion (48.5%) | Washout (40.3%) | Arterial phase hyperenhancement (38.4%) |
| Intrahepatic cholangiocarcinoma | Progressive hyperenhancement (58.2%) | Heterogeneous lesion (47.3%) | Infiltrative appearance (43.8%) | Nodularity (37.2%) |
| Colorectal carcinoma metastasis | Progressive hyperenhancement (67.2%) | Hypoenhancing core (52%) | Enhancing rim (46.9%) | N/A |

The model misclassified lesions with higher frequency when the radiological features were also misclassified. For the 12% of lesions that the model misclassified over 20 iterations, its PPV and Sn were reduced to 56.6% and 63.8% respectively. Furthermore, the feature that the model predicted with the highest likelihood was only correct in 60.4% of cases—by comparison, the feature that the model predicts with the greatest likelihood in correctly classified lesions was correct 85.6% of the time.

This effect was also observed when the feature identification metrics are grouped by lesion classes, as the model generally identified features most accurately for classes in which the lesion entity itself was classified with high accuracy. The model obtained the highest PPV for benign cyst features at 100% and lowest for CRC metastasis features at 61.2%. The model attained the highest sensitivity for hemangioma features at 96.1% and lowest for HCC features at 64.2%. The lesion classifier performed better on both cysts (Sn=99.5%, Sp=99.9%) and hemangiomas (Sn=93.5%, Sp=99.9%) relative to HCCs (Sn=82.0%, Sp=96.5%) and CRC metastases (Sn=94.0%, Sp=95.9%).

Feature Mapping with Weighted Activations

The features maps (shown in FIG. 15) were consistent with radiological features related to borders: enhancing rim and capsule/pseudocapsule, and a thin-wall yield feature maps that trace these structures. Additionally, the model's feature maps for hypoenhancing and hyperenhancing masses were well localized and consistent with their location in the original image: hypo-enhancing core/mass and nodularity had fairly well-defined bounds, as did arterial phase hyper-enhancement and hyperenhancing mass in delayed phase. Iso-intensity in venous/delayed phase was also well-defined, capable of excluding the hyperenhancing vessels in its map. In contrast, features describing enhancement patterns over time were more diffuse and poorly localized. There was slight misregistration between phases included in the hemangioma example, contributing to artifacts seen in the feature map for nodular peripheral hyperenhancement.

Feature Scoring with Influence Functions

The most relevant radiological feature for cavernous hemangiomas was progressive centripetal filling, with a score of 48.6% compared with 34.0% for hyperenhancing mass on delayed phase and 21.6% for nodular/discontinuous peripheral hyperenhancement. Thin-walled mass was usually a more relevant feature for classifying benign cysts than hypo-enhancing mass (67.1% vs. 46.6%, see Table 8). The most relevant feature for correctly classifying FNHs was iso-intensity on venous/delayed phase (79.4%), followed by arterial phase hyperenhancement (65.8%) and central scar (37.4%). The relevance scores for HCC imaging features were 49.5% for capsule/pseudo-capsule, 48.5% for heterogeneous lesion, 40.3% for washout, and 38.4% for arterial phase hyperenhancement. The relevance scores for ICC imaging features were 58.2% for progressive hyperenhancement, 47.3% for heterogeneous lesion, 43.8% for infiltrative appearance, and 37.2% for nodularity. The most relevant imaging feature for correctly classifying CRC metastases was progressive hyper-enhancement (67.2%), followed by hypoenhancing core (52.0%) and enhancing rim (46.9%).

Discussion

This study demonstrates the development of a proof of concept prototype for the automatic identification, mapping and scoring of radiological features within a DL system, enabling radiologists to interpret elements of decision-making behind classification decisions.

While DL algorithms have the opportunity to markedly enhance the clinical workflow of diagnosis, prognosis and treatment, transparency is a vital component. Indeed, it is impacted unlikely that clinicians would accept an automated diagnostic decision support without some measure of evidence to justify predictions. The method of identifying and scoring radiological features allows the algorithm to communicate factors used in making predictions. Radiologists can then quickly validate these features by using feature maps or similar interpretability techniques to check whether the system has accurately identified the lesion's features in the correct locations.

The CNN was able to identify most radiological features fairly consistently despite being provided with a small sample of lesions per class, in addition to being trained to perform an entirely different task. For many simple imaging features such as hyperenhancing or hypoenhancing masses, the model was able to accurately and reliably determine its presence, location, and contribution to the lesion classification. However, it had greater difficulty identifying or localizing features that consist of patterns over multiple phases than patterns that are visible from a single phase or constant across all phases. It struggled in particular on more complex features that may appear quite variable across different lesions such as infiltrative appearance, suggesting that these features are not well understood by the CNN or that more examples of these features need to be provided. By highlighting which radiological features the CNN fails to recognize, this system may provide engineers with a path to identify possible failure modes and fine-tune the model, for example, by training it on more samples with these features. A general relationship was observed between the model's misclassification of a lesion entity and its misidentification of radiological features, which could provide researchers and clinicians with the transparency to identify when and how a CNN model fails. If the model predicts non-existent imaging features, clinicians will be aware that the model has likely made a mistake. Moreover, this gives developers an example of a potential failure mode in the model. An interpretable DL system can be utilized as a tool for validation of imaging guidelines, particularly for entities which are uncommon or have evolving imaging criteria, such as bi-phenotypic tumors and ICCs. As shown in the results on feature scoring, the model tends to put greater weight on imaging features that have greater uniqueness and differential diagnostic power in the respective lesion class. An interpretable CNN could be initially presented with a large set of candidate imaging features. Then by selecting the imaging features with the highest relevance score output by the model, one could determine which features are most relevant to members of a given lesion class. This approach also addresses the need for more quantitative evidence-based data in radiology reports An interpretable DL system could help to address the large number of ancillary imaging features that are part of the LI-RADS guidelines and similar systems by providing feedback on the importance of various radiological features in performing differential diagnosis. With further refinements, the presented concepts could potentially be used to validate newly proposed ancillary features in terms of frequency of occurrence, by applying it to a large cohort and analyzing the CNN's predictions. Features that are predicted with low frequency or relevance could be considered for exclusion from LI-RADS guidelines. This could be a first step towards providing a more efficient and clinically practical protocol. An interpretable DL model could also enable the automated implementation of such complex reporting systems as LI-RADS, by determining and reporting standardized descriptions of the radiological features present. By enabling such systems to become widely adopted, there is potential for the reporting burden on radiologists to be alleviated, data quality to improve, and the quality and consistency of patient diagnosis to increase.

In summary, this study demonstrates a proof-of-concept interpretable deep learning system for clinical radiology. This provides a technique for interrogating relevant portions of an existing CNN, offering rationale for classifications through internal analysis of relevant imaging features. With further refinement and validation, such methods have the potential to eventually provide a cooperative approach for radiologists to interact with deep learning systems, facilitating clinical translation into radiology workflows. Transparency and comprehensibility are key barriers towards the practical integration of deep learning into clinical practice. An interpretable approach can serve as a model for addressing these issues as the medical community works to translate useful aspects of deep learning into clinical practice.

Example 3: a Probabilistic Approach for Interpretable Deep Learning in the Diagnosis of Liver Lesions The excellent performance of convolutional neural networks (CNNs) in the radiological diagnosis and prognosis of disease has generated increasing interest among radiologists in the translation of these methods for clinical use. However, the lack of transparency in a CNN's predication can lead to unpredictable or unexplained failure modes, a lack of accountability for such errors, and difficulty in integrating such models into existing workflows and frameworks for clinical decision-making and reporting. One solution for increasing such transparency is to should provide textual descriptions of the image-derived features that support the model's diagnostic or prognostic prediction, using terms that are familiar to radiologists and consistent with standardized radiological reporting systems such as the Liver Imaging Reporting And Data System (LI-RADS). This allows radiologists to critique the model's predictions and to supplement radiological features with other clinically relevant patient information in their reporting and decision-making.

Image captioning techniques and generative adversarial networks may be able to produce radiological descriptions from imaging but require large amounts of labeled data and additional architectural changes to the neural network. Interpretability techniques such as feature visualization and attribution provide useful insights into how a CNN reaches its prediction, but usually require its users to be knowledgeable about CNNs and may not be easily translated into clinical terms. This study aims to bridge the interpretability of CNNs to a non-technical audience and to allow model predictions to be aligned with existing diagnostic or prognostic criteria using techniques that do not require fully labeled datasets and that can be extended to any trained neural network.

Materials and Methods

Magnetic resonance imaging (MRI) was acquired from 1.5 T or 3 T MRI Siemens scanners in contrast-enhanced T1-weighted sequences with three time points post-contrast-administration (20 s, 70 s, 3 min) based on standard liver imaging protocol. Next, 494 lesions image volumes were obtained by cropping MRIs to the vicinity of each lesion and resampling this cropped region to a resolution of 32×32×16 voxels across all three time points. This dataset was divided into training and test sets, each consisting of six classes of liver lesions. The training dataset consisted of 434 lesion image volumes (64 simple cysts, 72 cavernous hemangiomas, 74 focal nodular hyperplasias, 99 hepatocellular carcinomas, 48 intrahepatic cholangiocarcinomas, and 77 colorectal cancer metastases), and the test dataset had 60 images (10 from each class). Each image volume was augmented by a factor of 256, using rotation, translation, scaling, flipping, interphase translation, intensity scaling, and intensity shifting.

A radiologist selected 16 radiological features comprising liver lesion characteristics that are observable on contrast-enhanced MRI and useful for differentiating between the six lesion types. Features with similar appearances were grouped, resulting in 14 final image-derived features of interest. For each feature, the radiologist selected up to 20 hepatic lesions in the training set that best exemplified each feature (e.g. shown in FIG. 6). The radiologist also labeled each image in the test set with the most prominent imaging features.

The CNN consisted of four 3D convolutional layers (192, 128, 128, 128 filters, all with kernel size 3×3×2), two max pooling layers and two fully connected layers (128 and 6 units respectively). The CNN used rectified linear units (ReLUs) in conjunction with batch normalization and 25% dropout. The CNN was trained to classify lesion images into one of the six lesion types with an Adam optimizer (lr=0.0001) using minibatches of four samples from each class.

Let $x \in \mathbb{R}^{32 \times 32 \times 16 \times 3}$ be the lesion image volume, $f\alpha \in \{0, 1\}$ be a binary indicator for the presence of a feature $\alpha$ in the image, and $h \in \mathbb{R}^{128}$ be the pre-ReLU values of the neurons in the first fully connected layer of the trained CNN. This layer was selected as the latent space because it was the last hidden layer of the CNN, and thus contains more sophisticated features that may correspond more directly with the imaging-derived features of interest. Estimating the probability $p(f\alpha=1|x)$ that the feature $\alpha$ is present in a given lesion image x was then sought. If an image-derived feature is useful for differential diagnosis, then a well-trained CNN should be able to encapsulate much of the information about its presence in each of its hidden layers. Hence, it was assumed that given h, x provides no information about $f\alpha$, i.e. $p(f\alpha|h,x)=p(f\alpha|h)$.

$$p(f_\alpha|x) = \int p(f_\alpha|h) p(h|x) d^{128}h \quad \text{Equation 1}$$

Using Bayes' Rule for $p(f_a|h)$, the following is obtained:

$$p(f_\alpha|x) = p(f_\alpha) \int \frac{p(h|f_\alpha) p(h|x)}{p(h)} d^{128}h \quad \text{Equation 2}$$

$$p(f_\alpha|x) = p(f_\alpha) \mathbb{E}_{h|x} \frac{p(h|f_\alpha)}{p(h)} \quad \text{Equation 3}$$

From Equation 3, $p(h|f\alpha=1)$ and $p(h)$ were evaluated at each value of h drawn from the probability distribution $p(h|x)$, where 256 samples from $p(h|x)$ were drawn by passing the augmented versions of x through the model to yield $h(i)$, $i=1, \ldots, 256$. For each i, the probability densities $p(h(i)|f\alpha=1)$ and $p(h(i))$ were estimated using a sparse kernel density estimation approach called regularization of derivative expectation operator (rodeo), which optimizes the bandwidth for each latent dimension by initializing it with a large value and iteratively decreasing it until the derivative of the probability density estimate with respect to the dimension's bandwidth becomes too large. As each image-derived feature is expected to influence only a small set of hidden neurons, this approach helps to identify these relevant neurons and perform sparse density estimation based on them, which reduces estimation error related to the curse of dimensionality. The local rodeo variant was used to calculate different bandwidths for each $h(i)$ using a Gaussian kernel and uniform baseline density. It was assumed that the values of h yielded by any lesion image in the training set can represent samples drawn from $p(h)$. Similarly, it was assumed that the values of h yielded by lesion images in the training set labeled with a feature $\alpha$ can represent samples drawn from $p(h|f\alpha=1)$. These samples were drawn using augmented images.

A simple estimate of $f_\alpha$ could be obtained based on the criterion $p(f_\alpha=1|x)>0.5$, since $\hat{f}_\alpha(x)=\text{argmax}_z p(f_\alpha=z|x)$ and $p(f_\alpha=1|x)=1$. However, the prior probability $p(f_\alpha)$ is difficult to estimate, and the empirical estimates of $p(f_\alpha|x)/p(f_\alpha)$ for a given feature ranged by many orders of magnitude depending on x, due to the curse of dimensionality. To address this, $\hat{f}_\alpha(x)$ was estimated using a criterion that does not depend on $p(f_\alpha)$. The criterion was also selected such that for all ten lesion images labeled with image-derived feature $\alpha$, which we denote $x_\alpha^{(j)}$, $j=1, \ldots, 10$, we guarantee $\hat{f}_\alpha(x_\alpha^{(j)})=1$. The estimation criterion was defined as:

$$\hat{f}_\alpha(x) = \begin{cases} 1 & \text{if } p(f_\alpha=1|x) \geq \min_j(p(f_\alpha=1|x_\alpha^{(j)})) \\ 0 & \text{otherwise} \end{cases} \quad \text{Equation 4}$$

Dividing both sides of the criterion by the prior probability $p(f_\alpha=1)$ yields:

$$\hat{f}_\alpha(x) = \begin{cases} 1 & \text{if } \mathbb{E}_{h|x} \frac{p(h|f_\alpha=1)}{p(h)} \geq \min_j \left( \mathbb{E}_{h|x_\alpha^{(j)}} \frac{p(h|f_\alpha=1)}{p(h)} \right) \\ 0 & \text{otherwise} \end{cases} \quad \text{Equation 5}$$

Figure 6:
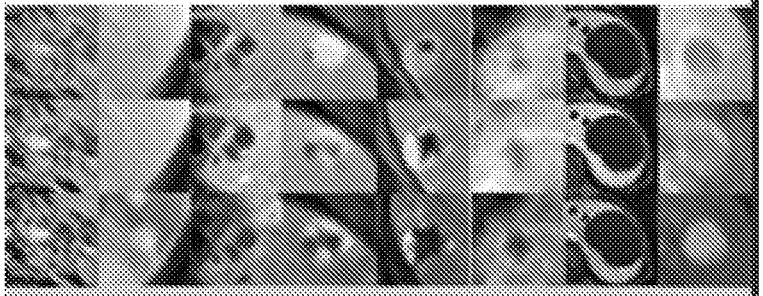
FIG. 6 depicts examples of labeled lesion images from tri-phasic MRI for the 16 radiological features, with associated lesion classes. Radiological features that appear similar were grouped, resulting in 14 image-derived features. HCC=hepatocellular carcinoma, ICC=intrahepatic cholangiocarcinoma, FNH=focal nodular hyperplasia, CRC=colorectal cancer.

Some imaging-derived features cannot coexist because they are always associated with different lesion types (shown in FIG. 6). In order to take this mutual exclusivity into account, Equation. 5 was adjusted to set $(f\_\alpha)\hat{\ }(x)$ to 0 if $\alpha$ is inconsistent with the most probable feature (ignoring the prior probability) $\beta=\text{argmax}_{\top}b \llbracket E\_(h|x) (p(h|f\_b=1))/(p(h)) \rrbracket$. The algorithm's performance with and without this adjustment was evaluated.

Results

The pretrained CNN had an overall lesion classification accuracy of 89.7% (538/600 lesions) across 10 different training iterations and 90.0% (54/60 lesions) on this particular test set. Each lesion in the test set was labeled with 1-4 imaged-derived features (2.6 on average, 154 in total). Across all features, the model had 76.8% precision (119/155 predicted features) and 77.3% (119/154 actual features) recall. The performance was slightly improved by the mutual exclusivity adjustment increasing precision to 81.1% (116/143) and reducing recall to 75.3% (116/154). On a lesion-by-lesion basis, the model had 83.3% precision and 75.7% recall on average.

It achieved the best performance at identifying simpler image-derived features such as arterial phase hyper-enhancement (precision=95%=18/19, recall=95%=18/19) while performing poorly on highly complex features such as infiltrative appearance (precision=20%=1/5, recall=25%=1/4). The model also incorrectly identified image-derived features more frequently when the lesion was misclassified. For the 6 lesions that the model misclassified, the precision and recall for their features were only 69.2% (9/13) and 56.3% (9/16) respectively, compared to the 82.3% (107/130) precision and 77.5% (107/130) recall for the 54 correctly classified lesions, suggesting that the quality of the CNN's explanations can provide information about the quality of its diagnosis.

CONCLUSIONS

This work demonstrates a probabilistic approach for analyzing the hidden layers of a trained CNN to accurately identify image-derived features of interest in an input image using sparsely labeled data. The correlation between the model's misclassifications of the lesion entity and its misidentification of radiological features could provide researchers and clinicians with the transparency to identify when and how the CNN model fails. If non-existent image-derived features are predicted, this gives engineers an example of a potential failure mode in the model, and physicians will also be aware that the model has likely made a mistake. This solution also enhances the potential for CNNs to be integrated into existing radiological workflows, where radiologists' clinical understanding of pathology and holistic view of the patient can be integrated with the CNN's advanced pattern recognition capabilities.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

The invention claimed is:

1. A computer-implemented method of identifying one or more clinical factors associated with an artificial intelligence prediction, the computer-implemented method comprising:
   applying a previously trained deep neural network to one or more images for a subject to produce a prediction, the previously trained deep neural network comprising a plurality of nodes;
   comparing outputs of the nodes to previously identified patterns of node outputs for a plurality of individual clinical factors;
   identifying which of the plurality of individual clinical factors are most correlated with the outputs of the nodes; and
   generating a contribution score for one or more of the plurality of individual clinical factors, the generating the contribution score comprising:
      iteratively removing one or more of the multilayer nodes associated with the previously identified patterns of node outputs for one of the plurality of individual clinical factors from the previously trained deep neural network to produce an altered deep neural network;
      applying the altered deep neural network to the one or more images to produce an altered prediction; and
      identifying a difference between the altered prediction and the prediction.

2. A computer-implemented method of identifying one or more clinical factors associated with an artificial intelligence prediction, the computer-implemented method comprising:
   applying a previously trained deep neural network to one or more images for a subject to produce a prediction, the previously trained deep neural network comprising a plurality of nodes;
   comparing outputs of the nodes to previously identified patterns of node outputs for a plurality of individual clinical factors;
   identifying which of the plurality of individual clinical factors are most correlated with the outputs of the nodes; and
   generating a contribution score for one or more of the plurality of individual clinical factors, the generating the contribution score comprising:
      quantifying the impact of removing the multilayer nodes associated with the previously identified patterns of node outputs for one of the plurality of individual clinical factors.

3. A computer-implemented method of identifying one or more clinical factors associated with an artificial intelligence prediction, the computer-implemented method comprising:
   applying a previously trained deep neural network to one or more images for a subject to produce a prediction, the previously trained deep neural network comprising a plurality of nodes;
   comparing outputs of the nodes to previously identified patterns of node outputs for a plurality of individual clinical factors;
   identifying which of the plurality of individual clinical factors are most correlated with the outputs of the nodes; and
   generating a contribution score for one or more of the plurality of individual clinical factors, the generating the contribution score comprising:
      quantifying the impact of removing one or more images having a single clinical factor on the prediction of the deep neural network.

4. A computer-implemented method of identifying one or more clinical factors associated with an artificial intelligence prediction, the computer-implemented method comprising:
   applying a previously trained deep neural network to one or more images for a subject to produce a prediction, the previously trained deep neural network comprising a plurality of nodes;
   comparing outputs of the nodes to previously identified patterns of node outputs for a plurality of individual clinical factors;
   identifying which of the plurality of individual clinical factors are most correlated with the outputs of the nodes; and
   generating one or more altered images illustrating regions of the one or more images associated with the one or more individual clinical factors correlated with the outputs of the multilayer nodes, the generating the one or more altered images comprising:
      identifying which of the multilayer node outputs are most correlated with each clinical factor;
      comparing the multilayer node outputs for the one or more images used for prediction relative to the multilayer node outputs for the one or more images correlated with individual clinical factors;
      designating each pixel or voxel in the one or more images used for prediction as significant to the one or more individual clinical factors if the multilayer node outputs associated with the pixel or voxel are correlated with the individual clinical factors and are comparable to the multilayer node outputs found in the one or more images correlated with individual clinical factors; and
      applying an overlay for each of the one or more individual clinical factors corresponding to the pixels or voxels designated as significant to the individual clinical factor.

5. A computer-implemented method of identifying one or more clinical factors associated with an artificial intelligence prediction, the computer-implemented method comprising:

applying a previously trained deep neural network to one or more images for a subject to produce a prediction, the previously trained deep neural network comprising a plurality of nodes;

comparing outputs of the nodes to previously identified patterns of node outputs for a plurality of individual clinical factors;

identifying which of the plurality of individual clinical factors are most correlated with the outputs of the nodes; and generating one or more altered images illustrating regions of the one or more images associated with the one or more individual clinical factors correlated with the outputs of the multilayer nodes, the generating the one or more altered images comprising:

iteratively removing one or more pixels or voxels from the one or more images to generate one or more stripped images;

reapplying the previously trained deep neural network to the one or more stripped images;

identifying one or more differences in outputs of the multilayer nodes for the one or more stripped images relative to the outputs of the multilayer nodes for the one or more images;

comparing the one or more differences to the previously identified patterns of node outputs for the plurality of individual clinical factors;

designating a pixel or voxel as associated with the one or more individual clinical factors correlated with the outputs of the multilayer nodes if the differences are correlated with the previously identified patterns of node outputs for the plurality of individual clinical factors; and applying an overlay corresponding to the pixels or voxels designated as associated with the one or more individual clinical factors.

\* \* \* \* \*